United States Patent [19]

D'Antonio

[11] Patent Number: 4,654,029

[45] Date of Patent: Mar. 31, 1987

[54] ELECTRONIC DRAINAGE SYSTEM

[75] Inventor: Nicholas F. D'Antonio, Liverpool, N.Y.

[73] Assignee: Howmedica, Inc., New York, N.Y.

[21] Appl. No.: 449,372

[22] Filed: Dec. 13, 1982

[51] Int. Cl.$^4$ .............................................. A61M 1/00
[52] U.S. Cl. ................................... 604/119; 128/771; 604/120
[58] Field of Search ............................... 604/118–121, 604/317–326, 65, 67, 51, 35; 128/760, 771; 251/304

[56] References Cited

U.S. PATENT DOCUMENTS

| | | | |
|---|---|---|---|
| 3,812,855 | 5/1974 | Banko | 604/120 |
| 3,934,561 | 1/1976 | Romann et al. | 123/494 |
| 4,019,535 | 4/1977 | Buckethal | 251/304 |
| 4,213,457 | 7/1980 | Lewis | 604/120 |
| 4,343,316 | 8/1982 | Jespersen | 128/771 |
| 4,366,051 | 12/1982 | Fischel | 210/134 |
| 4,369,785 | 1/1983 | Rehkopf et al. | 604/119 |
| 4,395,258 | 7/1983 | Wang et al. | 604/119 |
| 4,402,373 | 9/1983 | Comeau | 128/771 |

Primary Examiner—Edward M. Coven
Attorney, Agent, or Firm—D. Peter Hochberg

[57] ABSTRACT

A system for electronically monitoring and controlling the drainage of fluids from a body cavity, including transducers for measuring suction, suction air flow, patient air flow, patient negativity and the like, and displays for rendering measured values in legible form. Various valves for regulating pressure and flow rates are electronically controlled according to desired values and direct measurements of the respective parameters.

69 Claims, 10 Drawing Figures

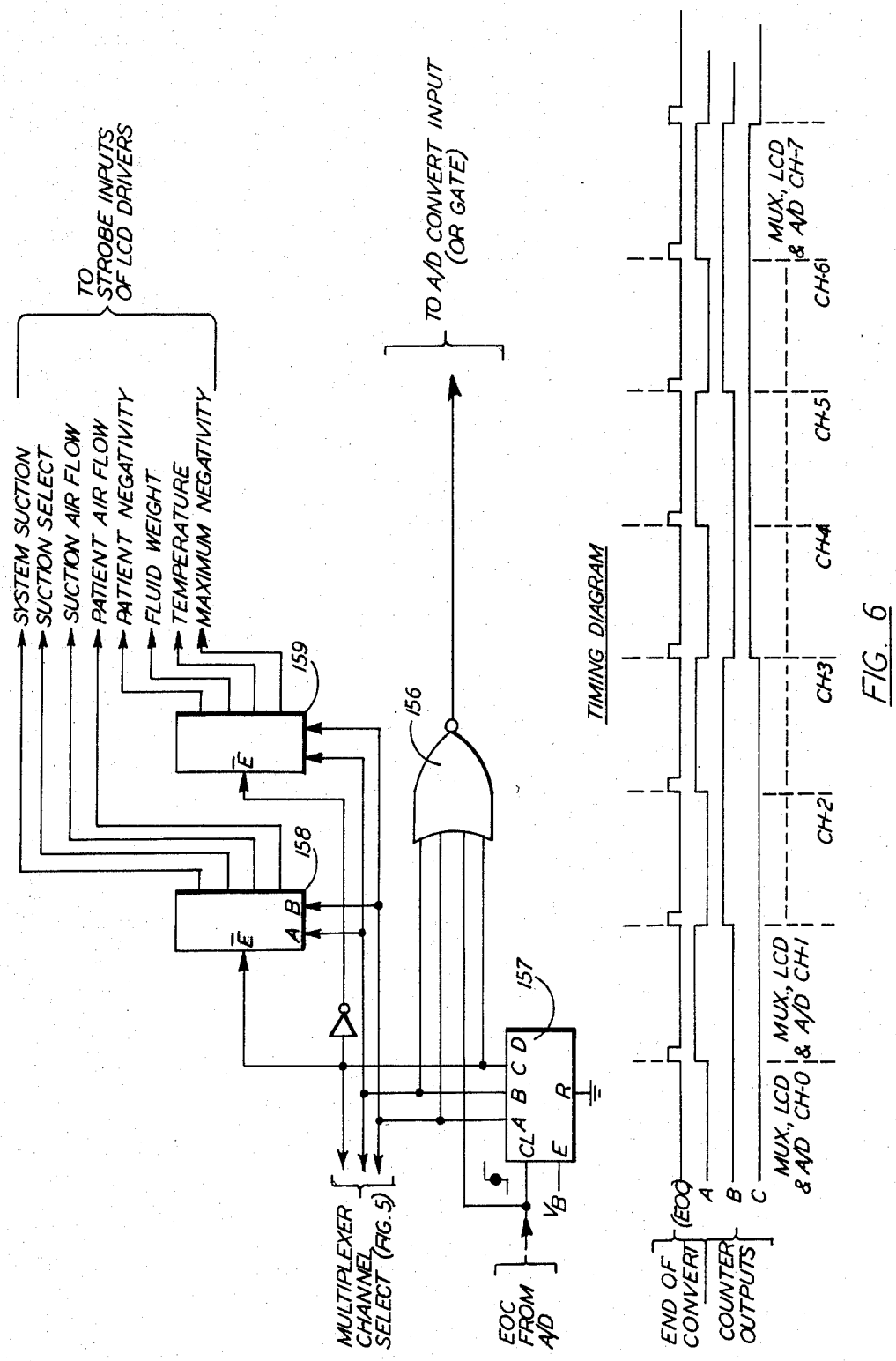

ELECTRONIC DRAINAGE SYSTEM

This invention relates to drainage systems, and in particular, to systems for draining fluids from cavities such as the pleural cavity.

BACKGROUND OF THE INVENTION

In some situations, and particularly in fields of medical treatment, it is important to drain a body cavity of extraneous fluids in a sanitary and precisely controlled manner. For example, a common result of chest surgery and the puncturing of the chest wall or of organs therein, is the accumulation of blood, water, gas and other fluids in the pleural cavity. The accumulation of fluids or air in the pleural cavity can be very dangerous and even fatal. In such conditions, it is vitally important that means be provided for evacuating such fluids and air from the pleural cavity and for assisting the lung to its normal expansion or reexpansion. Essentially, this calls for the application of a level of suction on the pleural cavity to withdraw the extraneous fluids and air, and help re-inflate the lung once it has collapsed. For many years, a standard apparatus performing the evacuation process was an underwater seal drainage system known as the "3-bottle set-up". The 3-bottle set-up consists of a collection bottle, a water seal bottle and a suction control bottle. A catheter runs from the patient's pleural cavity to the collection bottle, and the suction bottle is connected by a tube to a suction source. The three bottles are connected in series by various tubes to apply a predetermined suction to the pleural cavity to withdraw fluid and air and discharge same into the collection bottle. Gases entering the collection bottle bubble through water in the water seal bottle. The water in the water seal also prevents the back flow of air into the chest cavity.

The 3-bottle set-up lost favor with the introduction of an underwater seal drainage system sold under the name "Pleur-evac" in 1966 by Deknatel Inc., the predecessor of the Deknatel Division of Howmedica Inc. U.S. Pat. Nos. 3,363,626; 3,363,627; 3,559,647; 3,683,913; 3,782,497; 4,258,824; and Re. 29,877 are directed to various aspects of the Pleur-evac system which has been marketed over the years. The Pleur-evac system provided improvements that eliminated various shortcomings of the 3-bottle set-up. These improvements have included the elimination of variations in the 3-bottle set-up that existed between different manufacturers, hospitals, and hospital laboratories, such variations including bottle size, tube length and diameter, stopper material and the like. Various inefficiencies and dangers have existed in the 3-bottle set-up resulting from the many separate components and the large number (usually 16 or 17) of connections, such as pneumothorax which may result from the loss of the water seal in the water seal bottle if suction were temporarily disconnected, and possible build-ups of positive pressure which could cause tension pneumothorax and possible mediastanal shift. Another serious shortcoming of the 3-bottle set-up is danger of incorrect connection and the time necessary to set the system up and to monitor its operation.

Among the features of the Pleur-evac system which provide its improved performance are employment of 3-bottle techniques in a single, pre-formed, self-contained unit. The desired values of suction are established by the levels of water in the suction control bottle and the water seal bottle, which levels are filled according to specified values prior to the application of the system to the patient. A special valve referred to as the "High Negativity Valve" is included which floats closed when the patient's negativity becomes sufficient to threaten loss of the water seal. Also, a "Positive Pressure Release Valve" in the large arm of the water seal chamber works to prevent a tension pneumothorax when pressure in the large arm of the water seal exceeds a prescribed value because of suction malfunction, accidental clamping or occlusion of the suction tube. The Pleur-evac system is disposable and helps in the battle to control cross-contamination.

Despite the advantages of the Pleur-evac system over the 3-bottle set-up and the general acceptance of the device in the medical community, there has remained a continuing need to improve the convenience and performance of chest drainage systems and to render such systems very compact. Underwater seal drainage systems as described above require the filling of manometer tubes to levels specified by the physician prior to being connected to the patient and the hospital suction system. Although it is conceivable that such filling could be performed at a manufacturing facility prior to shipment, as a practical matter this would not suffice because frequent adjustments are needed according to the different values of patient suction as dictated by the attending physician. Moreover, the presence of fluid in the various tubes could result in damage to the system during shipment such as because of freezing temperatures or because of leakage. In addition, accuracy of present underwater drainage systems is limited in that the filling of the manometers and the reading of the various gauges must be done visually by observing the liquid level in the respective chambers. A reduction in size of the system would offer such benefits as ease of use, ease of storage, less expensive shipping costs, and the reduction in the obstruction between the patient, his or her visitors and the medical staff.

Furthermore, the present underwater seal drainage systems are not conducive to incorporation in larger systems which perform other functions besides that of draining the pleural cavity and enabling the monitoring of a limited number of physical factors such as various pressure measurements. It would be a great advantage to have a drainage system which could be incorporated with other systems for the purpose of monitoring various important occurrences associated with the patient, such as temperature, respiration, pressure differentials, the quantity and flow rate of fluids drained from the patient and the like.

The use of electronic technology in conjunction with the monitoring of the drainage of body fluids is not entirely new. For instance, U.S. Pat. No. 4,206,727 describes a urological drainage monitor including an electronic timing system for periodically altering the liquid flow path into a series of receptacles for indicating the characteristics of fluid collected in each time period. However, systems for electronically controlling independent variables such as imposed suction and fluid flow and for electronically measuring the characteristics of gas flow and liquid flow associated with their drainage from the body was heretofore unknown.

SUMMARY OF THE INVENTION

The present invention provides an electronic drainage system for draining of liquid and gases from a cavity such as the pleural cavity, while providing means for making any of a number of measurements and for generating accurate and easily comprehendable readings without the need to resort to manometer tubes or other fluid gauges. The invention contemplates both a comprehensive system for controlling the flow of fluids from the pleural cavity or the like, through a simple hook-up between the patient and a suction system, while monitoring any of various physical characteristics and indicating such measurements on readily readable displays, such characteristics including: effluent temperature, effluent volume, effluent weight, patient negativity pressure, maximum negativity, patient air flow rate, suction, suction air flow and the like. A preferred circuit for performing the foregoing functions includes various transducers which can further be used to regulate the desired suction setting and to measure various air flow rates while providing automatic and precise control of the regulated parameters, and circuitry connected to an effluent collection chamber for repeatedly measuring and emptying the chamber to provide the drainage function as well as the measurement functions of the fluids associated therewith. Multiplex circuitry is preferably provided for automatically reading the various measuring devices and for displaying relevant information in an easily understandable form. The invention on a less comprehensive scale comprehends a combination of electronic and mechanical components for measuring and displaying values for air flow, suction, patient negativity and maximum negativity. The invention in its preferred form includes fluid contaminatable portions which are disposable after use.

DESCRIPTION OF THE DRAWINGS

FIG. 6 is a schematic diagram of a multiplexer select and LCD driver decoder network used with the system of FIG. 5;

DETAILED DESCRIPTION OF THE PREFERRED EMBODIMENTS

Figure 1:
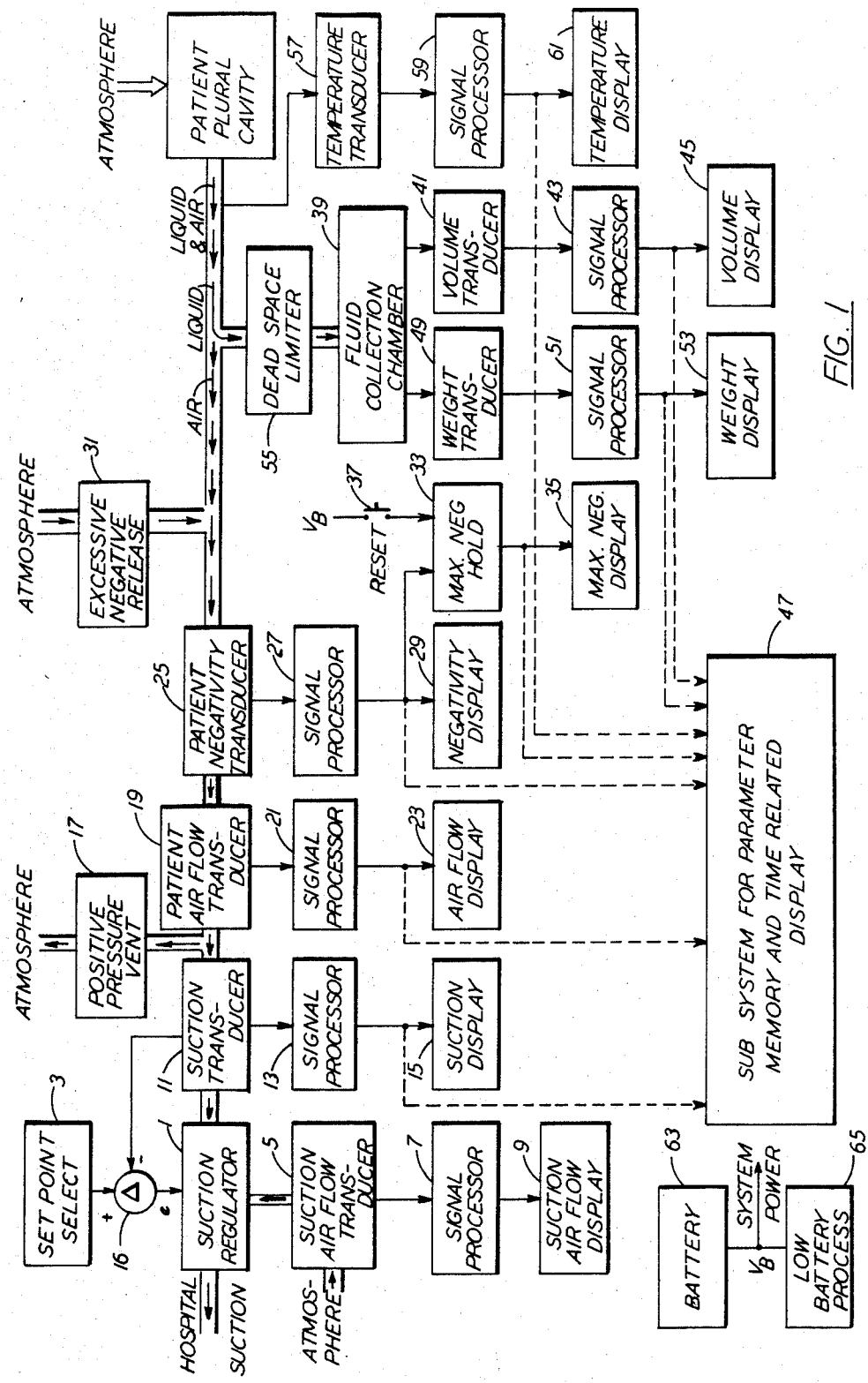
FIG. 1 is a schematic diagram of a comprehensive system according to the invention.

Turning first to the comprehensive system shown schematically in FIG. 1, it will be observed from the discussions that follow that the system provides a variety of information and fluid drainage controls while involving but two fluid connections, one to the patient and one to a suction line such as one associated with a hospital suction system. A suction control means in the form of a suction regulator 1 includes means for controlling the suction applied to the system. Such means can conveniently comprise an electrically or pneumatically driven motor for varying the size of an orifice in the suction line through which air can be admitted from the atmosphere to atmospheric pressure. The level of suction is established by the adjustment of a set point select 3, which can conveniently be manually set by an attendant according to appropriate instructions. Such a manual setting could be made by means of a dial or by the depression of a correct sequence of buttons on a numerical array, or the like. A common setting would be $-20$ cm. $H_2O$ pressure. A means for monitoring the flow of air into the suction system to arrive at the desired suction value is accomplished by a monitoring means shown in FIG. 1 as an air flow transducer 5. Signals generated by a suction air flow transducer 5, indicating the amount of air flow, are processed in a signal processor 7 to which transducer 5 is connected, and the value is displayed on a suction air flow display 9.

The actual negative pressure in the suction line is measured by a suction transducer 11, and this transducer generates a signal reflective of that value and transmits it to a signal processor 13 which processes the signal and in turn transmits it to a suction display 15 where that value can be observed. Suction transducer 11 also transmits a signal of the actual negative pressure to a difference or error signal generating device 16. Device 16 generates a signal "e" whose magnitude is a function of the selected value of the set point device 3 and the real value represented by the signal generated by suction transducer 11. The drive motor of regulator 1 rotates in the correct direction in response to the signal "e" generated by device 16 to vary the orifice through which ambient air is admitted to the suction line, until the difference between the signals generated by devices 3 and 11 is zero or nearly zero, depending on whether a type 1 or type 2 control loop (as discussed below) is used. Suction regulator 1 is very important because it compensates for differences between the suction systems of different hospitals or other facilities in which the system of FIG. 1 would be used, as well as compensating for significant changes within a given system as the number of users connected to the suction line changes. The suction applied to the patient is selected by the physician according to the physical condition or nature of the illness of the patient, and it is important that variations in this pressure be kept to a minimum to avoid further damage to the lung or pleural space. As noted above, display 15 renders the output of transducer 11 in a legible form, which can be digital, a bar graph, a meter or the like.

It is very important that pressure build-up in the pleural space be prevented such as in the event of a failure of the vacuum system. Therefore, a positive pressure vent 17 is provided which can be either a mechanical or electronic device, although mechanical devices of simple construction would be most economical under the preferred embodiment, particularly if venting is restricted to fixed values of differential pressure. The vent could be established whenever a positive pressure of, for example, 1 cm. $H_2O$ more positive than atmospheric occurs, which is indicative of a failure in the vacuum system.

A patient air flow transducer 19 is located to measure the flow rate of air and other gases in the conduit from the patient. When the system is perfectly sealed, any air flowing through the conduit is coming from the pleural space, and the flow rate is a function of both the volume of the air leak and the suction pressure as established by the setting of set point select 3. A signal processor 21 is electrically connected to transducer 19 to convert the signal from the transducer to a form needed by an air flow display 23. The readout of display 23 can conveniently be provided in units of liters per minute.

Transducer 19 preferably operates in conjunction with a one-way valve. As the volume of the air leak decreases, a natural consequence is the development of a negative pressure in the pleural space, and this negative pressure is generally referred to as "patient negativity". If a patient develops a negative pressure greater than that of the suction system, the valve associated with transducer 19 closes to assure the absence of a reverse in the pleural space.

A patient negativity transducer 25 is also provided in the air conduit. The latter transducer measures the negative pressure in the pleural space. If the valve associated with transducer 19 is open, transducer 25 senses a negative pressure that is very close to that of the suction system, differing only by the loss downstream at element 19. However, when the valve associated with transducer 19 closes, it is important to know what level of negativity the patient is achieving. Therefore, a signal processor 27 is electrically connected to transducer 25 and to a negativity display 29. If the patient negativity pressure sensed by transducer 25 and displayed on display 29 warrants an adjustment, the pressure loss that occurs across element 19 can be adjusted. Imposing a pressure loss in transducer 19 means that the physician wants the patient to develop a pressure before allowing any of the air to be released from the pleural space into the suction system.

Frequently, as the patient is healing, the level of negativity which develops cycles up and down. Since larger levels of negativity may occur while the attendant monitoring the system is away from the patient, it may be useful for the physician to know what maximum level of negative pressure was actually attained. Such high levels of negativity may also occur if the tube inserted into the pleural space, such as for withdrawing air and accumulated fluids, becomes clogged with blood clots, damaged tissue or the like. In order to clear the blockage, the attendant "milks" the tube in an attempt to reopen it, however, this procedure often causes high values of momentary negativity on the patient. In order to determine that this has happened and to what extent, a maximum negativity hold device 33 is electrically connected to signal processor 27 and is so devised as to record and store negativity values up to the level permitted by an excessive negativity release or safety valve 31. The stored value is displayed on display function 35. In the event the maximum negativity reaches a dangerous level, excessive negativity release 31 is provided as a safety valve which allows atmospheric air to enter the unit when a predetermined maximum occurs. The safety valve 31 prevents additional damage due to excessive negative pressures. A maximum negativity reset switch 37 allows the attendant to clear the old maximum in order to record a new one which may occur at a later time. This feature has a decided advantage over existing drainage systems which, in some cases, display the occurrence of a high negative pressure by using a water catching depression or cup; however, it is a one time mechanism because once filled it cannot be reset.

A collection chamber 39 is provided for receiving fluids which are withdrawn from the injured area such as the pleural cavity. Unlike present drainage systems wherein the face of the collection chamber is calibrated in cubic centimeters (cc's) of fluid and which is normally marked to indicate the particular level of liquid present at specified times, in the electronic system shown in FIG. 1, the volume of liquid is monitored electronically with a volume transducer 41. A signal processor 43 is electrically connected to transducer 41 and to a volume display 45. Volume display 45 shows the physician in a quickly and readily understandable way how much liquid has been lost by the patient. A computer memory 47 is electrically connected to the output of signal processor 43 for storing the time history of this collection along with all of the other parameters as indicated by the dotted lines electrically connecting the respective signal processors with this memory. The memory 47 thus provides a complete, recoverable history of the illness and its therapy. A weight transducer 49 is electronically connected with fluid collection chamber 39 for weighing the fluid in the chamber as a function of time. A signal processor 51 is electronically connected with the transducer and to a weight display 53. The weight transducer and associated processor and display, enable the measurement and recording of the parameter fluid versus time, a parameter neither measured nor recorded under prior drainage systems. The system of FIG. 1 thus provides means for measuring and recording in real time, i.e., a running computation of weight or volume, and from this a determination of fluid density, fluid composition, and other analyses (such as spectral, enzyme, blood content of the fluid, and the like) to be made. Furthermore, by electronically connecting the signal processor 51 with computer memory 47, the computer can give the physician a very valuable measure of the actual loss of blood as well as providing other computer calculatable information.

Were fluid collection chamber 39 simply connected directly to the fluid flow conduit from the cavity being drained, there would be a necessary delay in the time for air flow to commence because there would have to be a sufficient buildup of air pressure within the empty part of collection chamber 39 to overcome the loss at the valve associated with transducer 19. Therefore, a device referred to as a dead space limiter 55 is provided between the fluid flow conduit from the patient cavity being drained and the fluid collection chamber 39. Device 55 blocks the large volume of the empty collection chamber from the small volume of the air flow path. The limiter fills with liquid from the cavity, dumps it into a receiving bottle and recloses the fluid passageway. Not only does dead space limiter 55 block the empty part of collection chamber 39 from the air flow path, but it can also be used to record total volume based on its capacity and the number of times it has been emptied.

In order to measure the temperature of fluid leaving the patient's cavity and to record that temperature over time, an electronic thermometer in the form of a temperature transducer 57 is electronically connected to the fluid conduit from the cavity. The transducer or sensor 57 is advantageously mounted directly to the catheter structure that is inside the cavity wall. A signal processor 59 is electrically connected to transducer 57, and the temperature display 61 is connected to the processor. This arrangement provides for the automatic and accurate measurement and recording of temperature, and is more efficient than the prior procedure wherein a nurse makes temperature readings from time to time on a "conventional" thermometer. The signal processor can be electronically connected to computer memory 47 for the recording function.

The system is energized by appropriate means such as a battery 63. A battery monitoring device 65 can be provided for monitoring the state of the battery and for generating a warning signal on one or more displays of the system when the battery output falls below a predetermined voltage level. The battery voltage is indicated by the symbol $V_B$.

The system of FIG. 1 is thus a comprehensive unit having a very flexible format capable of obtaining, recording, displaying and evaluating a variety of data for accurately monitoring the state of a patient whose pleural or other cavity is being drained. Device 47 is a storage and computing system having enough memory for storing the desired amount of information for the expected life of the device. This computer and memory system can include such accessories as a cathode ray tube (CRT), chart recorder, printer, tape or disc or any other readout that will give a permanent running history of the parameters being measured. The system can be modified to independently record data for more than one catheter should drainage be performed in the pleural cavity of a patient both of whose lungs have been damaged, or if more than one catheter is placed in a single pleural cavity (such as one for gas and one for liquids), and the system additionally could be centrally located to collect and store data from numerous locations for more than one patient. The system, when adapted to operate in conjunction with drainage in several locations, can be operated on a time-share basis, while still possessing the ability to provide an on command CRT, chart recorder or printer history of each of the inputs, all of this with a minimal number of attendants. An especially useful readout, for example, would show not only the total amount of fluid lost, but also the amount lost during each hour of the treatment so that the degree of improvement or decline could readily be determined and made a permanent part of the patient's record. Other attendant controlled display means could be used as well.

FIG. 1 shows fluid flow patterns for both air flow and liquid flow. The system of FIG. 1 thus makes the following measurements and effects the following controls: (1) system suction and control; (2) patient air flow; (3) patient negativity and maximum negativity; (4) fluid temperature; (5) fluid volume; and (6) fluid weight.

Preferred embodiments for performing the foregoing functions are shown in FIGS. 2-6 and are described in the following paragraphs.

Figure 2:
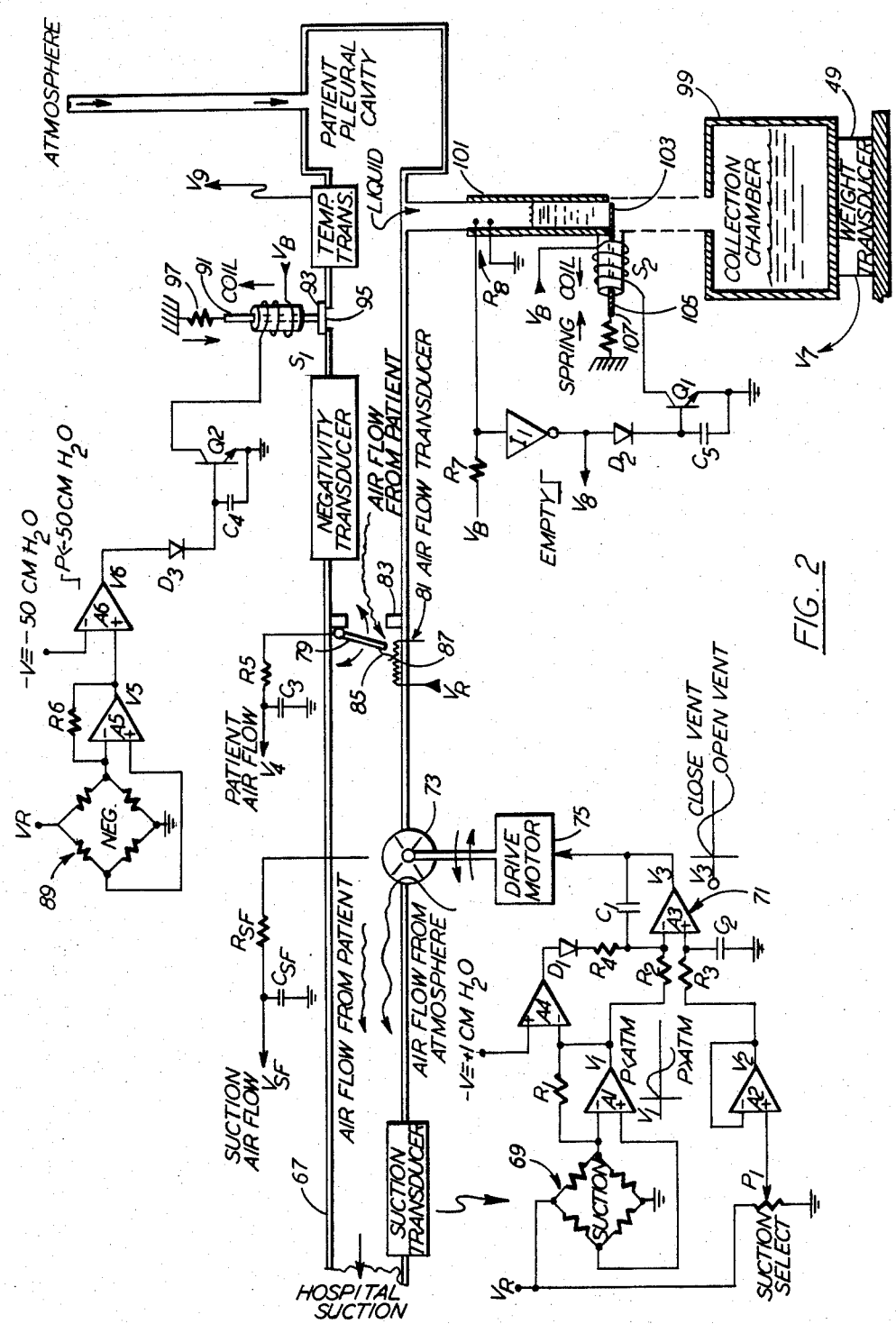
FIG. 2 is a circuit diagram showing the transducers and control devices incorporated in the system of FIG. 1.
Figure 3:
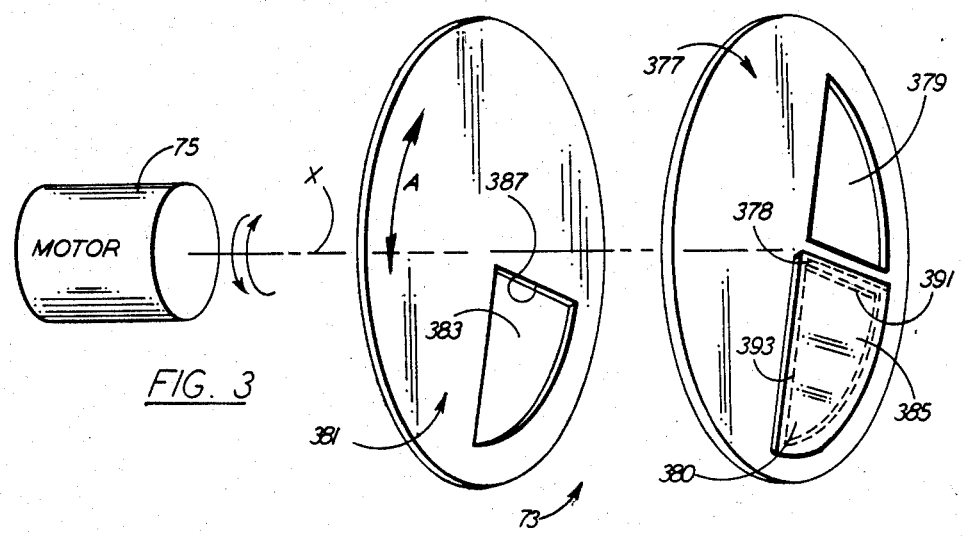
FIGS. 3 and 4 are perspective and cross-sectional, schematic detailed views, respectively, of the suction air flow valve shown in FIG. 2.
Figure 4:
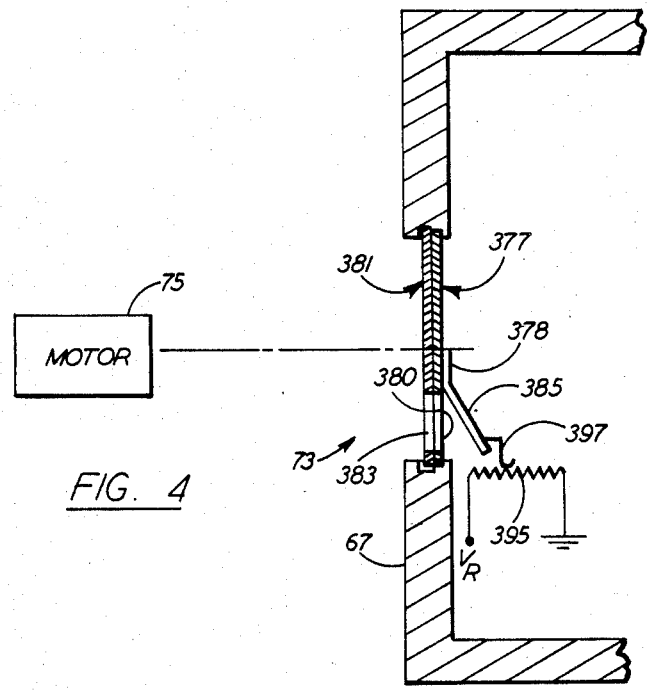

FIG. 2 shows a control loop for suction regulation. Suction transducer 11 is mounted in an air flow line or suction conduit 67 connected to a hospital suction source (not shown) when the unit is put into operation. Suction transducer 11 is shown as a resistive bridge 69 comprising four resistors. Two of the resistors are connected together and to a reference voltage source $V_R$, and the other two resistors are connected together and grounded at their juncture. One of the resistors connected to voltage source $V_R$ and one of the grounded resistors are connected to the positive input of an amplifier $A_1$, and the juncture of the other resistor connected to $V_R$ and the other grounded resistor are connected to the negative input of amplifier $A_1$. (Although suction transducer 11 is shown as a resistive bridge, other transducer techniques could be used as well, such as a diaphragm-actuated resistive potentiometer, a capacitative device, an inductive device such as a LVDT-linear voltage displacement transducer or a light sensor.) Amplifier $A_1$ generates a voltage signal $V_1$ from the small variations in resistance detected by the bridge 69. Amplifier $A_1$ also provides a low impedance source for the resulting signal. It is contemplated that bridge circuit 69 is a conventional unit which could be purchased with an integral amplifier $A_1$. The output $V_1$ of amplifier $A_1$ is the electrical equivalent of the pressure within suction line 67. A potentiometer $P_1$ includes a resistor connected at one end to the voltage reference source $V_R$ and grounded at its other end, and a probe is connected to the positive port of an amplifier $A_2$. The voltage established by potentiometer $P_1$ is manually set by an attendant according to the desired value of suction. Amplifier $A_2$ is a voltage follower, and the voltage versus suction relationship from the upper part of potentiometer $P_1$ should be identical to that of amplifier $A_1$. The output of voltage follower $A_2$ is shown as $V_2$. The outputs of devices $A_1$ and $A_2$ are connected respectively to resistors $R_2$ and $R_3$, which are in turn connected to the negative and positive inputs of a differential integrator 71. Differential integrator 71 comprises an amplifier $A_3$, resistors $R_2$ and $R_3$, a capacitor $C_1$ connected across the negative input and the output of amplifier $A_3$, and a capacitor $C_2$ connected from the positive input to ground.

Suction regulator 1 from FIG. 1 is shown as a suction flow valve 73. Valve 73 is preferably an air flow flap valve which is operated by a drive motor 75 and functions as a variable orifice for flow line 67. The construction of valve 73 is shown in detail in FIGS. 3 and 4. The valve includes a stationary member shown as a disc 377 fixed in the wall of conduit 67 and having a pair of orifices 379 and 380 shown as equal partial sectors of disc 377, a coaxial disc 381 mounted for rotation in the direction of arrow A on the common axis x of the two discs and having an orifice 383 of equal size and shape to orifices 379 and 380, and a flap valve 385 mounted on disc 377 over orifice 380. Flap valve 385 functions to measure the flow of air through orifice 380; it is pivotally mounted near axis x on disc 377 for movement between a closed position where it closes orifice 380, and an open position, the amount which corresponds to the volume of air flow through orifice 380. Flap valve 385 is attached to disc 377 at location 378 by appropriate means such as rivets or other fasteners, welding, or the like. The valve is preferably biassed to its closed position by means of springs, the resiliency of the material from which it is made, gravity or the like. Valve 73 is preferably mounted in a vertical plane hanging vertically downward so that closure of flap valve 385 can be gravity controlled if so desired. Valve 73 regulates the suction in conduit 67 by regulating the flow of atmospheric air into the conduit. Disc 381 is movable among various positions, and is in sliding engagement with disc 377 to prevent air flow between the discs. In order to prevent any air flow through valve 73, such as when conduit 67 has not yet achieved the desired valve of suction, disc 381 is rotated to put orifice 383 out of any alignment with either of orifices 379 and 380, and with the body of disc 381 closing orifices 379 and 380. Intermediate amounts of air flow through valve 73 are obtained by the partial overlapping of orifices 383 and 380 while the body of disc 381 closes orifice 379. That is, the intermediate air flow needed to control suction to the selected valve is achieved by the movement of an edge 387 of orifice 383 across orifice 380 between edges 391 and 393 of orifice 380. As noted above, flap valve 385 measures the flow of air through orifice 380. This measurement is accomplished by means of a grounded resistence bar 395 to which a reference voltage $V_R$ is applied, and a conductive feeler 397 which rides across bar 395 as flap valve 385 pivots with changes in the flow of air through orifice 380. Changes in the resistance at bar 395, and consequently in the pick-off voltage of feeler 397, reflect the air flow through orifice 380. The output signal is impressed across a low pass filter comprising resistor $R_{SF}$ and capacitor $C_{SF}$, provided to filter out extraneous signal variations, to provide a suction air flow signal $V_{SF}$ which is transmitted to processor 21 and to display 23. The suction detection and readout devices tell the attendant when the hospital suction is set in the correct range for efficient system operation. Disc 381 is rotatable by the drive shaft of motor 75, the operation of which is controlled by the output voltage $V_3$ of differential integrator 71. When the output voltage $V_2$ of voltage follower $A_2$ exceeds the output $V_1$ of amplifier $A_1$, the suction in flow line 67 has failed to reach the value selected by the attendant in the adjustment of potentiometer $P_1$. Therefore, differential integrator 71 integrates $(V_2-V_1)$ in a positive direction, and a positive output $V_3$ results. $V_3$ is applied to drive motor 75, and the motor turns in a direction to reduce the opening established by valve 73, and thus reduces the amount of atmospheric air leaking into the line. With the reduction in the size of the opening, the suction level in line 67 increases, causing voltage $V_1$ to increase until voltage $V_1$ equals or exceeds voltage $V_2$, at which time the foregoing operation reverses itself. The behavior of this loop as it approaches a steady state condition depends upon the response speed of its components and the damping or time constraints of the entire loop. Differential integrator 71 acts to reduce its output $V_3$ to zero in the steady state condition; therefore, this is defined as a Type II loop in control theory terminology. A graph showing the variation of $V_3$ with time is shown adjacent to integrator 71. Of course, all of the rules for loop stability as dictated by the techniques of Bode, Nyquist or Root Locus must be obeyed to avoid the occurrence of an unstable oscillatory condition.

A feedback resistor $R_1$ is connected across the negative input and the output of amplifier $A_1$. Resistor $R_1$ and the output of amplifier $A_1$ are also connected to the negative input of a comparator $A_4$. The positive input of comparator $A_4$ is connected to a voltage source whose negative value corresponds to a predetermined positive pressure. The function of comparator $A_4$ is to provide the positive pressure vent referred to as device 17 in FIG. 1. A negative value of the output $V_1$ of amplifier $A_1$ indicates that the pressure in line 67 is greater than atmospheric pressure; when the value $V_1$ becomes more negative than the voltage applied to the positive input of comparator $A_4$, which value can for example correspond to $+1$ cm. $H_2O$, the output of comparator $A_4$ changes to its high state which sends a positive pressure vent signal to the negative port of differential integrator $A_3$. When this occurs, the output $V_3$ of differential amplifier $A_3$ goes full negative, forcing valve 73 to open to its fullest extent (so that orifices 383 and 379 are completely aligned), thus allowing the excess air pressure in line 67 to escape unimpeded into the atmosphere. This action eliminates the influence of flap valve 385 which will normally close with the occurrence of reverse pressure to actually prevent the release of the positive pressure that must be eliminated. Other means for venting such positive pressure could be used; for example, a solenoid valve driven by the output of comparator $A_4$ could be used as well. However, the use of an orifice already available simplifies the mechanical design of the system. A diode $D_1$ is connected to the output of comparator $A_4$ to protect differential amplifier $A_3$ against negative voltages from comparator $A_4$.

Although the means for rotating disc 381 is shown as an electrical drive motor in an analog loop, this means could also be a stepper motor as part of a digital control loop. The approach selected would depend on the desired resolution of the correction, power consumption, size, cost and speed.

The electrical signal for patient air flow is shown as a voltage $V_4$ and the electrical equivalent of the suction air flow $V_{SF}$. The value of voltage $V_4$ is established by a patient air flow transducer 81, similar to suction air flow transducer 73. Transducer 81 itself includes, in addition to a hinged flap 79, a stop 83 positioned so that flap 79 is rotatable between a vertical position in which it abuts stop 83 and a position to the left of vertical in which the orifice is virtually wide open. When the pressure downstream of the flap (i.e., to the left as shown in FIG. 2) exceeds that upstream of the flap, flap 79 abuts stop 83 and blocks passage 67 so that no reverse air flow occurs. A conductive feeler 85 is attached to the free end of flap 79 for riding across a resistive bar 87 as flap 79 moves. Bar 87 is grounded at one end and has the reference voltage $V_R$ applied to the other end. As flap 79 moves to its closed position, the resistance and the pickoff voltage of transducer 81 are zero. When the pressure upstream of flap 79 exceeds that downstream thereof, flap 79 rotates clockwise according to the pressure differential (and air flow) across it. The resulting variation in resistance and pickoff voltage on resister 87 are representative of the air flow, and the electrical output of transducer 81 is processed accordingly.

A resistor $R_5$ and a grounded capacitor $C_3$ form a low pass filter connected to flap 79 and are provided to smooth out any unwanted variations in the signal reflective of air flow, such as that component of the total imposed by the patient's breathing. As indicated earlier, the purpose for providing a flap 79 of transducer 81 and the positive pressure release function of comparator $A_4$ is to provide protection against the dangerous situation of reverse air flow to the patient when a pressure greater than atmospheric exists in flow line 67. These functions are redundant and serve to back each other up.

Patient negativity transducer 25 from FIG. 1 is shown in its preferred form as a bridge circuit 89 in FIG. 2. Bridge circuit 89 includes a pair of resistors connected to a reference voltage $V_R$, one of the latter resistors and a third resistor connected to the negative input of an amplifier $A_5$, the latter resistor and a fourth resistor connected to ground, and the first and fourth resistors connected to the positive input of amplifier $A_5$. A feedback resistor $R_6$ is connected across the negative input and the output of amplifier $A_5$. The output of amplifier $A_5$ is the electrical equivalent of patient negativity and is shown as a voltage $V_5$. The function and arrangement of bridge 89, amplifier $A_5$ and their associated connections are similar to those associated with bridge 69 and amplifier $A_1$. A negativity comparison means in the form of a comparator $A_6$ has connected at its input port the output of amplifier $A_5$, and the negative input of comparator $A_6$ is connected to a voltage source which corresponds to a predetermined level of pressure such as $-50$ cm. $H_2O$. Comparator $A_6$ changes state and generates a negativity signal when the negative pressure exceeds that to which the predetermined value applied to the negative input corresponds. A transistor $Q_2$ is connected to the output of comparator $A_6$. The output of voltage comparator $A_6$ is shown as a voltage $V_6$. A solenoid $S_1$ is connected to the collector of transistor $Q_2$ as well as to the system power $V_B$. Solenoid $S_1$ includes a movable rod 91 having a valve 93 at a free end for closing a port 95 in air flow line 67. A spring 97 biases rod 91 to a position where valve 93 closes port 95. When the negative pressure on comparator $A_6$ exceeds the predetermined level shown as −50 cm. $H_2O$, the high state of voltage $V_6$ turns on transistor $Q_2$, the coil of solenoid $S_1$ is energized, and rod 91 is moved upwardly to open port 95 so that atmospheric air bleeds into line 67 to release excess negativity. When the excess negativity is released, spring 97 forces valve 93 into the closed position. Diode $D_3$ and capacitor $C_4$ are used to hold valve 93 in the open position long enough to avoid a chattering condition.

Preferred embodiments of the dead space limiter, the fluid collection chamber, and the electronic elements associated with the fluid collection chamber are shown in FIG. 2. Weight transducer 49 can take any of a number of forms since the measurement which it must make is straight-forward and not particularly delicate. It is shown sitting on a fixed platform supporting a collection chamber 99 which is a preferred embodiment of fluid collection chamber 39 in FIG. 1. Collection chamber 99 could be hung on a hook attached to transducer 49; alternatively, the weight of liquids withdrawn from the patient's cavity could be measured using a weight transducer operatively associated with the dead space limiter and volume monitor described below. In either event, a transducer of the type described with regards to bridge circuits 69 and 89 would be appropriate devices for the weight transducer.

Dead space limiter 55 and volume transducer 41 from FIG. 1 are depicted in their preferred form as a "dead space limiter and volume monitor" 101. Device 101 comprises a cup of known volume having a horizontal sliding trap door bottom 103. A spring 107 of solenoid $S_2$ is provided for biasing door 103 to its closed position until a predetermined quantity of liquid accumulates in device 101, after which the door opens and fluid empties into collection chamber 99. Alternatively, solenoid $S_2$ could be a rotary solenoid to efficiently open the trap door in a rotary rather than a sliding motion. An electronic circuit is provided for use in conjunction with device 101. This circuit includes a pair of contact points separated by a distance shown as $R_8$, the points being connected respectively to ground, and to a resistor $R_7$ and to the input of an inverter $I_1$. When device 101 is full of liquid, a resistance conductive path very much lower than that of resistor $R_7$ is provided between the foregoing conductive points across the place shown as $R_8$. System power $V_B$ is applied to resistor $R_7$. The output voltage of inverter $I_1$ is a voltage $V_8$ whose high state corresponds to volume monitor 101 being filled to the level of $R_8$. The output port of inverter $I_1$ is connected to a diode $D_2$ which is in turn connected both to the base of a transistor $Q_1$ and to a capacitor $C_5$. The emitter of transistor $Q_1$ is connected to ground and to capacitor $C_5$. The collector of transistor $Q_1$ is connected to the coil of a solenoid $S_2$, and power is supplied to the circuit from the system power supply as indicated by $V_B$. Door 103 is part of a solenoid rod 105 of solenoid $S_2$ and it is biased to the closed position by a spring 107. When the coil is energized, rod 105 is urged against the bias of spring 107 to open trap door 103.

As noted, when device 101 is full of liquid, $R_8$ forms a low resistance resistor, this resistance being much lower than that of resistor $R_7$. When the resistance of $R_8$ is low, the output $V_8$ of inverter $I_1$ goes high, thus turning on transistor $Q_1$ to energize the coil of solenoid $S_2$ to momentarily open trap door 103. When dead space limiter and volume monitor 101 empties, the contacts of resistor $R_8$ are cleared, $I_1$ goes low and spring 107 closes door 103. Diode $D_2$ and capacitor $C_5$ assure that enough charge exists to hold transistor $Q_1$ in the ON state long enough for the cup of device 101 to completely empty. The output voltage $V_8$ is connected to a counter, and whenever $V_8$ goes through a low-to-high transition as shown on the graph adjacent inverter $I_1$, the counter keeps a running accumulation of the number of times the cup of device 101 empties, and therefore the total volume collected. As indicated earlier, when trap door 103 is closed, the large volume of collection chamber 99 is disconnected from the small volume of the air line coming from the patient pleural cavity, thereby avoiding a large delay before air flow will begin. It should be noted that a second trap door at the top of collection chamber 101 could be used to totally separate collection chamber 99 from air line 67 by closing when solenoid $S_2$ opens, but this probably represents more complexity than reasonably needed.

Temperature transducer 57 generates an electrical signal $V_9$ which corresponds to the temperature of the fluid being withdrawn from the cavity. A variety of temperature sensitive devices can be used for performing this function. Some examples are thermocouples, thermistors, semiconductor detectors such as the LM 135 series integrated circuit temperature sensors marketed by National Semiconductor Inc.

Figures 5, 5A:
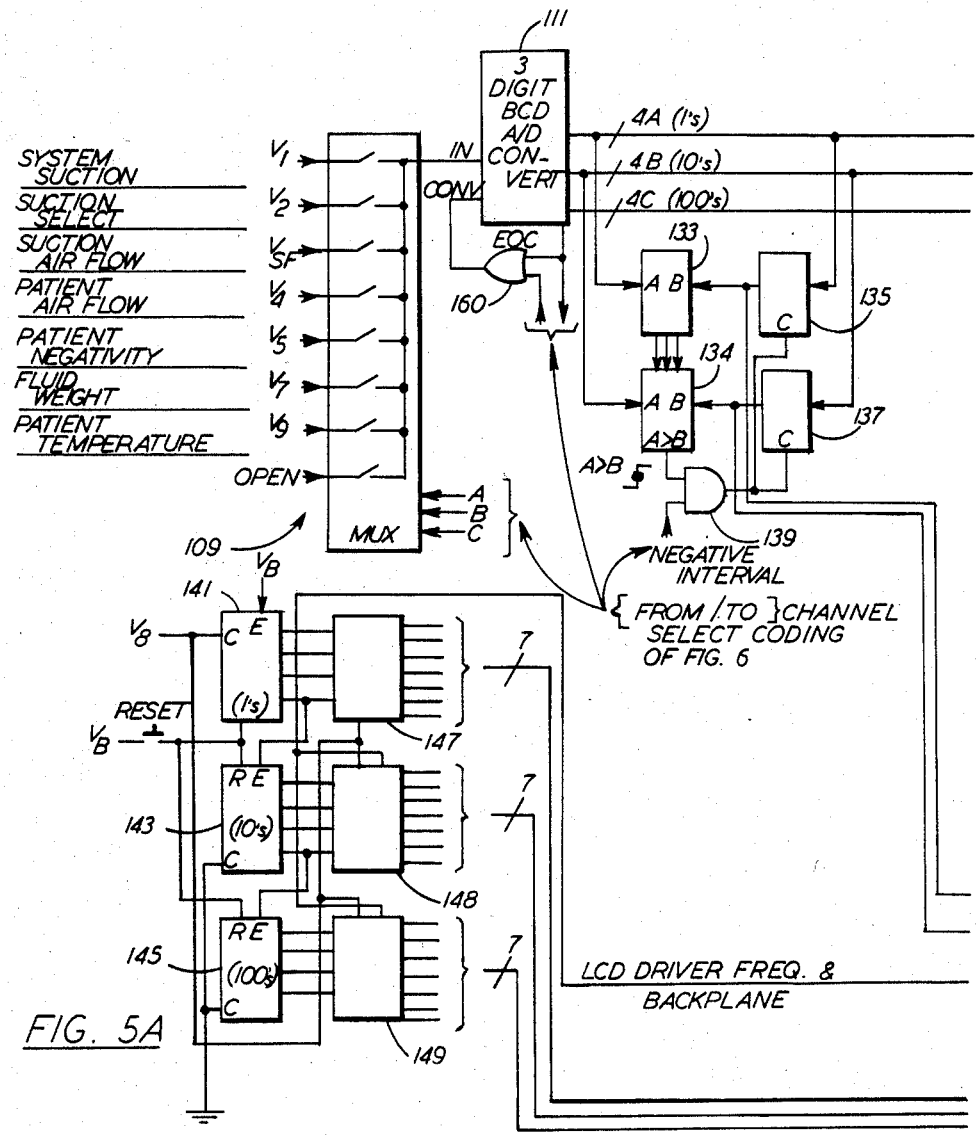
FIG. 5 shows the relationship of FIGS. 5a and 5b.
FIGS. 5a and 5b combined show in schematic form circuitry for performing the information retrieval and display functions for the system of FIG. 1.
Figure 5B:
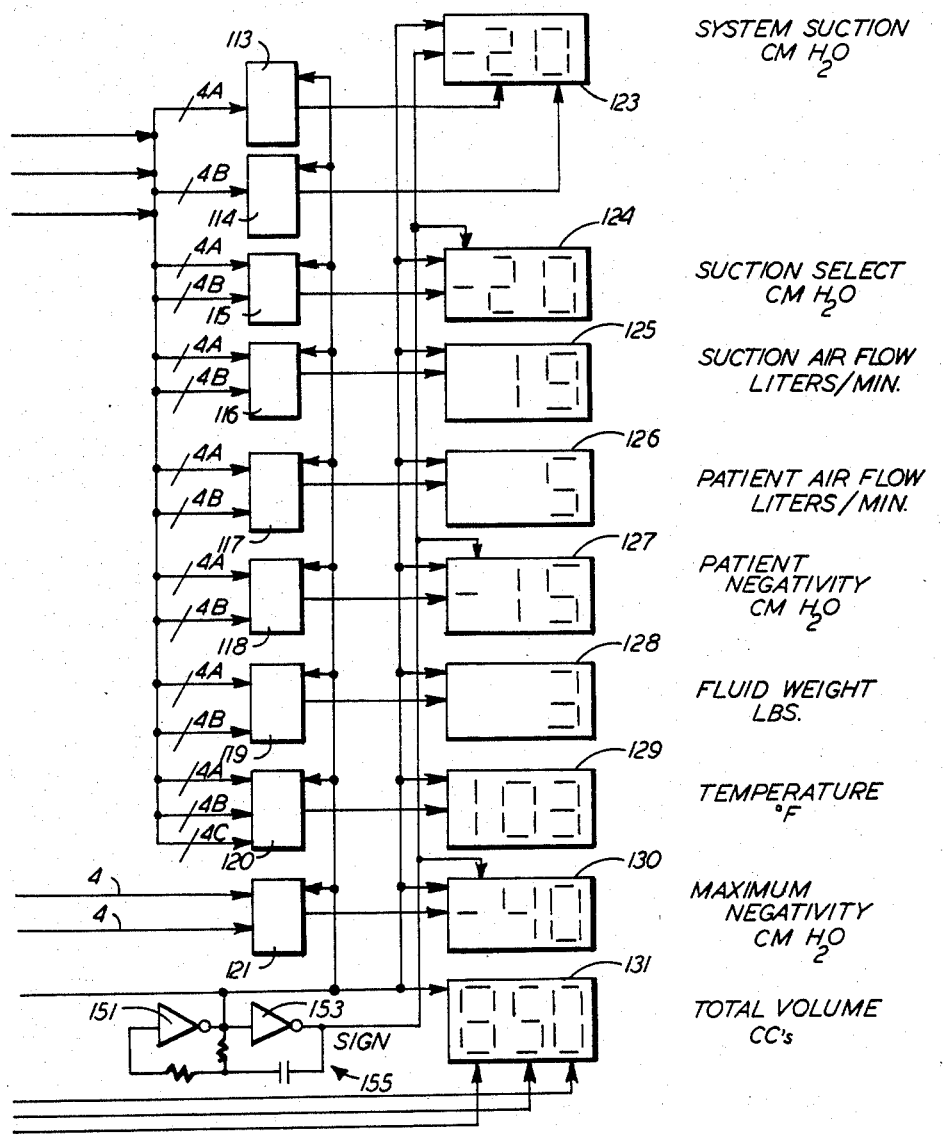

FIG. 5 shows the preferred system for processing the various values detected and controlled by the system of FIG. 2, and further shows how these values are displayed in a meaningful manner. In the interest of incorporating an economical system format, all of the analog signals generated by the system of FIG. 2 are converted to their binary coded decimal (BCD) equivalents with a multiplexer 109 and a single analog-to-digital (A/D) converter 111. Since seven separate analog signal outputs from the system of FIG. 2 are to be processed ($V_1$, $V_2$, $V_{SF}$, $V_4$, $V_5$, $V_7$ and $V_9$), an appropriate multiplexer chip such as the standard CMOS CD 4051 can be used to transmit all 7 signals to A/D 111. For the system shown in FIG. 5, a particularly advantageous A/D is a BCD three-digit A/D converter such as the DATEL ADC-EK 12D. Other such devices are available, and the specific device selected can be made according to such factors as speed, resolution, accuracy, size, power and cost. Although the latter device is relatively slow at a ten millisecond conversion time, it is in fact more than adequate for the present application. Analog Devices, Inc. also offers converters that will suffice.

Alternatively, digital voltmeter chips such as the National Semiconducter ADD3501 could be used. However, a different circuit design would be needed since the display driver (an LED in this case) is included on the chip and the digits of a particular display are multiplexed internally.

The output ports of A/D 111 are electrically connected to the inputs of a series of LCD drivers 113–121. Appropriate LCD drivers are CD4056 drivers. These devices contain data latches and the logic to convert the four-bit BCD input code to the 7-segment code for the digital display. The respective drivers are electrically connected to liquid crystal display (LCD) devices 123-131 for indicating the respective values measured. As noted, one CD4056 LCD driver is used for each digit, so that the data readout for a particular parameter is always present and only changes when a new conversion occurs. The storage of new information is explained below with regard to FIG. 6.

The A-word of a pair of digital comparators 133, 134 are connected to the ones and tens output lines of A/D converter 111, and the output of latches 135 and 137 are connected to the B-word of the foregoing comparators. These comparators and latches are used to detect and store the maximum value of patient negativity. Each new digital value for negativity is compared to the prior maximum stored in the latches, this being defined as the "B-word". If the new value, defined as the "A-word", is greater than the old value, then the A greater than B (A>B) output port of the comparators goes high. The low-to-high transition of A>B goes to the clock input C of the respective latch and the new data is stored. As soon as A equals B or A is less than B (A≦B), the A>B output goes low again in preparation for the next comparison. An AND gate 139 at the clock input of the respective latches assures that the data transfer can only occur for comparisons made during the negativity interval. Preferred digital comparators 133 and 134 are CD4063 digital comparators and preferred latches are CD4042 latches. The preferred AND gate 139 is a CD4081 AND gate.

A 16-bit BCD counter 141-145 is provided for receiving the signal $V_8$ generated by inverter $I_1$ in FIG. 2. Each time the cup of device 101 empties, voltage $V_8$ goes from low to high, and a one count increase in counter 141 occurs. An appropriate counter for this system is a CD4518 dual binary coded decimal (BCD) counter. The display for the volume collected is preferably in cubic centimeters; therefore, if the container of 101 is greater than 1 cubic centimeter, a preconditioned multiple count is needed to make the CD4518 output compatible with the actual value of the container. As previously, the display driver chips are preferably CD4056 devices. These chips are shown by identification numbers 147-149.

When using LCD displays as suggested above, a back plane frequency is needed. This is provided by a pair of inverters 151 and 153 which are connected to form an oscillator 155 which provides two oscillitory signals 180° out of phase with each other. Accordingly, the output of inverter 151 is connected to the input of inverter 153 and this output and input are connected to display driver chips 147-149, 113-121, and the back plane of the LCD displays. A pair of resistors are connected across inverter 151, and one of the latter resistors and a capacitor are connected across inverter 153, which together form the oscillator 155. The output of inverter 153 is connected to the in-phase segment (i.e., never on, such as decimal points, etc.) of the various LCDs 123-131, associated with driver chips 113-121. Preferably, inverters 151 and 153 are CD40106 inverters. When the digit segments are in phase with the back plane frequency, the segment is OFF (i.e., the output of inverter 153 providing this function); if the two frequencies are out of phase, the segment comes ON. The display driver chips, as indicated above, are preferably CD4056 chips, provide this logic.

FIG. 6 shows circuitry for the display storage logic for the system of FIG. 5. The graph associated with the circuitry shows the correct timing for display storage, multiplexer 109 and A/D converter 111. A four input NOR gate 156, which is preferably a CD4002, is driven by the output lines of a system timing counter 157, preferably a 4-bit binary CD4520 which also drives the channel select inputs of MUX 109 and a pair of decoders 158 and 159, which are preferably CD4555 "1 of 4" decoders. The output of NOR gate 156 is connected to an OR gate 160 at the input of A/D converter (FIG. 5) and assures an initial power-up conversion by giving a high level to the converter input; this happens because counter 157 comes ON with an "all zeros" output causing NOR gate 156 to be high which triggers A/D 111 so that the channel zero data of multiplexer 109 is immediately converted and stored. At the end of each conversion, A/D 111 generates an "end of convert" (EOC) pulse which increments counters 157. As indicated above, the outputs of counters 157 are decoded by multiplexer 109, and the next channel is selected. At the same time, they are decoded in "1 of 4" decoders 158, 159 to instruct LCD driver chips 113-121 as to where the newly converted signal should be held in storage. The pair of decoders 158, 159 does this by providing a different output line in the high state for each of the possible combinations of the A,B and C outputs from the 157 counters. The EOC pulse also returns to the convert input port of the converter 111 to initiate the conversion of the next MUX input. The timing diagram at the bottom of FIG. 6 shows the sequence and timing for these events.

Figure 7:
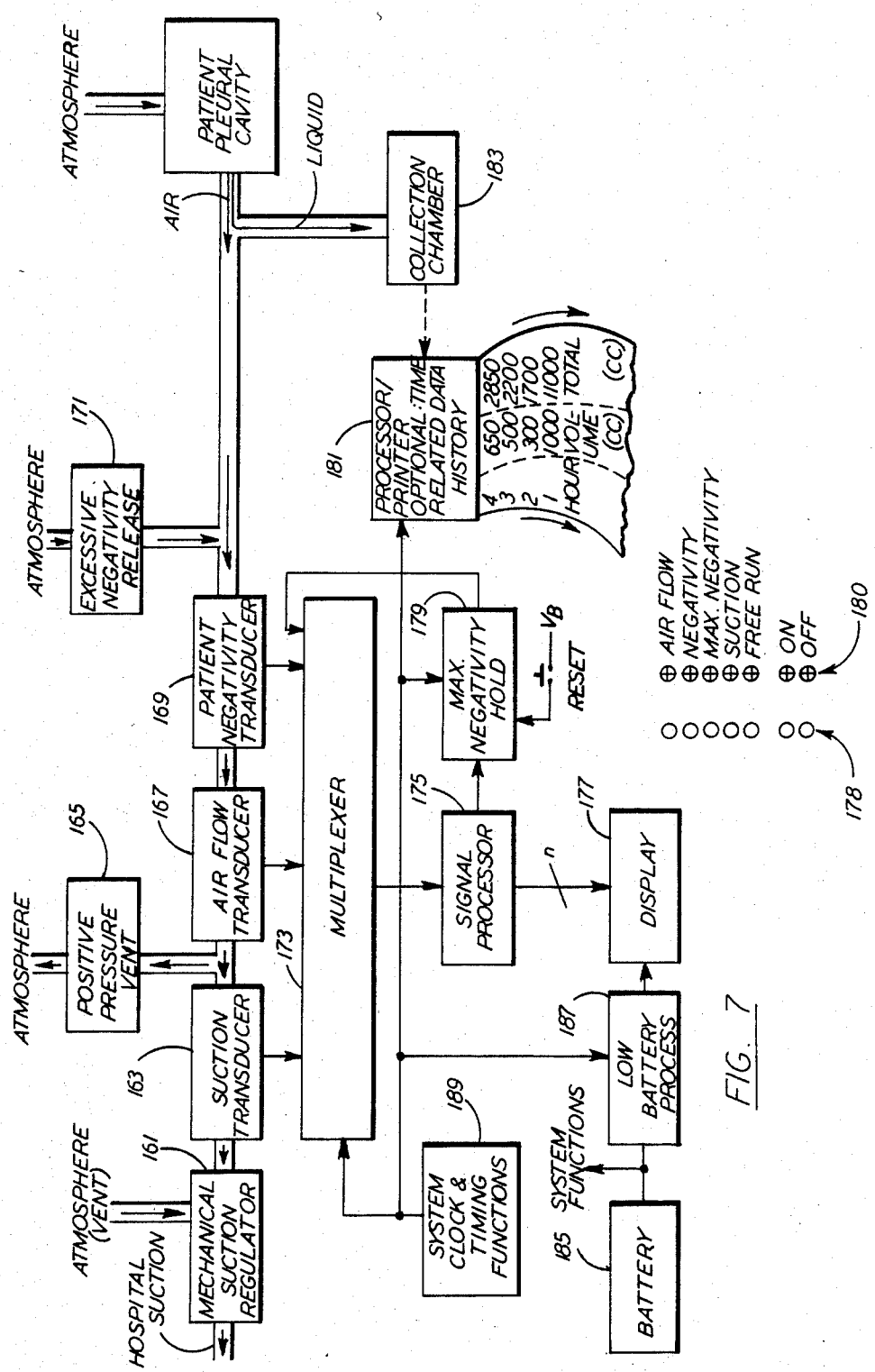
FIG. 7 shows in schematic form a block diagram for a single multiplexed display which is less comprehensive than the system of FIG. 1.

FIG. 7 shows another comprehensive drainage system similar to that of FIG. 1 but capable of performing fewer functions. Nevertheless, it should be noted at the outset that the system of FIG. 7 is more comprehensive than any mechanical or other drainage system presently known. It also should be noted that the system of FIG. 7 is capable of being supplemented with additional devices for monitoring and controlling values in addition to those shown in the diagram. Also, the system of FIG. 7 incorporates various mechanical portions in addition to the electronic portions. An air flow line is shown extending from the pleural cavity of a patient. A mechanical regulator 161 includes a variable orifice in the air flow line for controlling the pressure in the line. As explained with regard to FIG. 2, it is contemplated that the desired pressure is obtained by increasing or decreasing the tension on a spring which controls a valve to vary the opening in the orifice. As indicated previously with regards to FIG. 1, the readout of system parameters is normally cyclic; however, in FIG. 7 each of the values monitored will automatically appear in a sequential manner on a single display unless, of course, a given value is locked in place so that the display of that parameter remains in the readout for an extended period of time.

The system of FIG. 7 includes a mechanical suction regulator 161, an electronic pressure measuring device in the form of a suction transducer 163, a mechanical positive pressure vent 165, an electronic air flow measuring device in the form of an air flow transducer 167, an electronic patient negativity measuring device in the form of a patient negativity transducer 169, and a mechanical excessive negativity release 171. Transducers 163, 167 and 169 are connected to a multiplexer 173. A signal processor 175 is electrically connected to multiplexer 173 for receiving signals from each of the transducers and for processing the signals and then transmitting them to a display 177. The functioning of the foregoing devices and the nature of other devices in the system are described below.

Suction regulator 161 is preferably a simple spring-loaded mechanical regulator which can be adjusted to a desired pressure by increasing or decreasing the spring tension on a valve-controlled orifice. Since the pressures in the air flow line and the readout of the system parameters are normally cyclic, it is advantageous to lock a specific parameter on display 177 while necessary adjustments are made. Accordingly, display 177 should have some means including a manually controlled switch or button for performing such a locking function for each parameter. A set of parameter or mode select buttons 178, which include an ON button and an OFF button, and parameter or mode indicator devices 180 (shown as lights) for indicating the parameter whose value is being shown on display 177, are therefore provided. Hence, to set the desired suction, the suction transducer's output is locked on display 177, the regulator knob of suction regulator 161 is then adjusted until the pressure measured by transducer 163 and shown on display 177 equals the desired value.

Positive pressure vent 165 is also preferably mechanical and can be made from a "ball" filled orifice. When the pressure in the air flow line exceeds atmospheric pressure by some specified amount, such as 1 cm. $H_2O$, the pressure differential is great enough to lift the ball from the orifice to vent atmospheric air into the system. In this way the internal pressure is controlled to a given amount above atmospheric.

Air flow transducer 167 is similar in function to air flow transducer 19 of FIG. 1. Thus, air flow transducer 167 only allows air to flow in the direction of the suction source and blocks the path if the pressure differential is reversed. Patient negativity transducer 169 is similar to transducer 25 in FIG. 1. Transducer 169 gives a reading very nearly the same as that of suction transducer 161 when the air flow passage is open; however, it reads patient negativity whenever the patient's pressure is further below atmospheric than that of the suction system, i.e, when the foregoing pressure differential is reversed. Excessive negativity release 171 is a mechanical device such as a ball filled orifice, and it vents the system to atmospheric air when patient negativity exceeds a predetermined maximum value.

As mentioned earlier, multiplexer 173 selectively receives and transmits electrical signals from transducers 163, 167 and 169, and transmits them to signal processor 175 and display 177. A maximum negativity hold device 179 is connected to an output of signal processor 175, and it has an output connected to multiplexer 173. This device is provided for retaining information in either analog or digital form depending on the exact circuitry used; however, if done in digital form, a D/A converter would be provided, unless of course, multiplexer 173 is a digital device.

A processor/printer 181 can be provided to make a real time readout of the amount of liquid collected during predetermined time periods such as hourly, or over the course of the illness or treatment, while also providing the cumulative total from the beginning of the measuring period. The printer could be a detachable unit which is removed from the disposable part of the system and returned to the manufacturer for sterilization, and subsequently re-used. Processor/printer 181 is shown operatively connected to a fluid collection chamber 183.

The system of FIG. 7 is powered by a battery 185, which is connected to the various devices requiring system power as indicated by the arrow at the output of the battery. A low battery process device 187 corresponds to a similar device 65 in FIG. 1; that is, it monitors the condition of the battery and produces a warning signal via display 177 if voltage $V_B$ falls below a predetermined minimum. A system clock and timing device 189 is connected to multiplexer 173, processor/printer 181, low battery process device 187 and maximum negativity hold device 179 for transmitting timing signals to the respective electronic devices. A maximum negativity reset switch corresponding to switch 37 in FIG. 1 is preferably provided to enable an attendant to clear the prior maximum value of patient negativity so that a new maximum can be recorded. While a printer is shown, it is contemplated for a low cost disposable version of FIG. 5 that the liquid level in collection chamber 183 be marked by an attendant to give an indication of volume versus time for the collected liquids.

Figures 8, 8A:
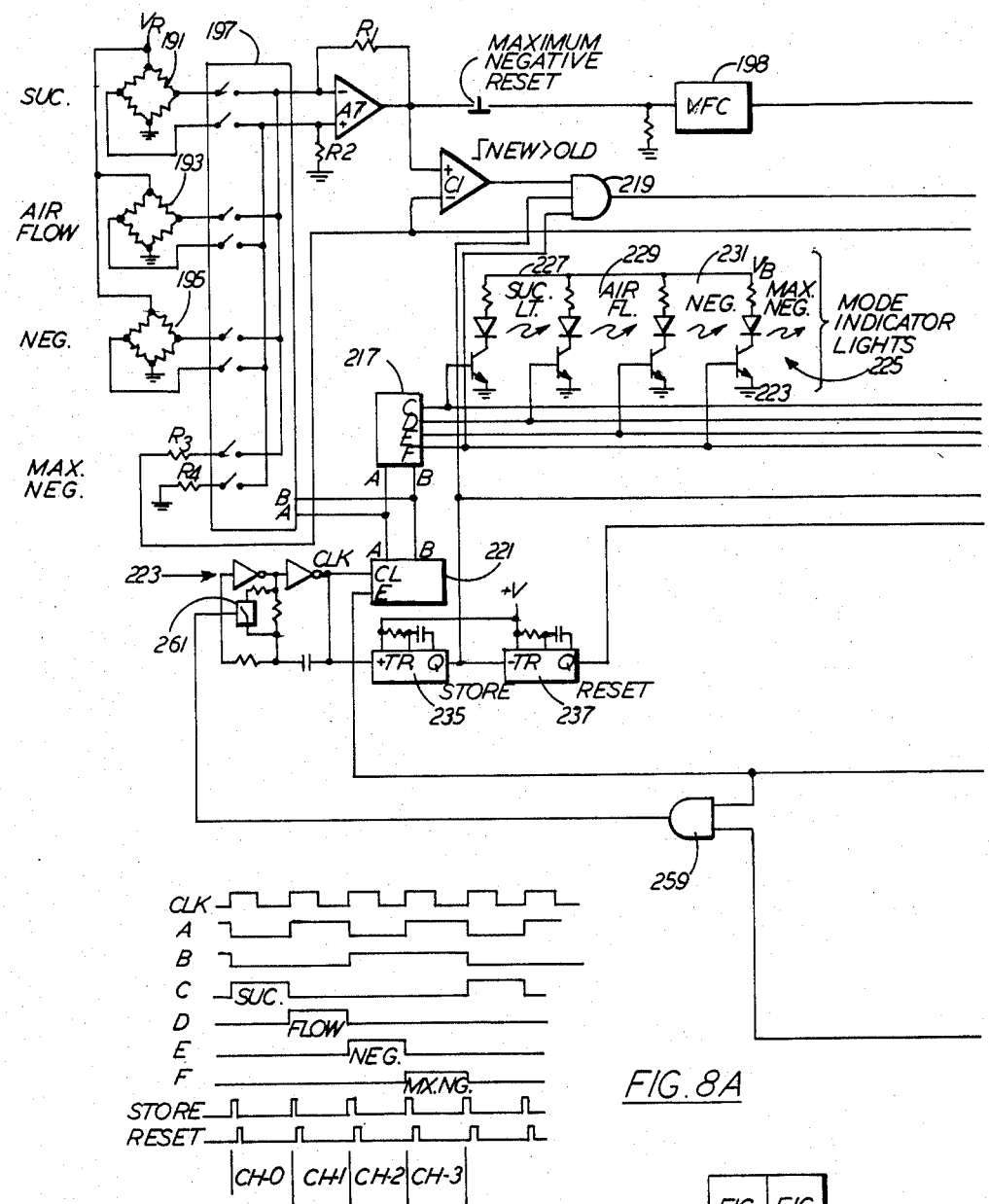
FIG. 8 shows the relationship of FIGS. 8a and 8b.
FIGS. 8a and 8b combined show a circuit diagram of a system according to the embodiment of FIG. 7.
Figure 8B:
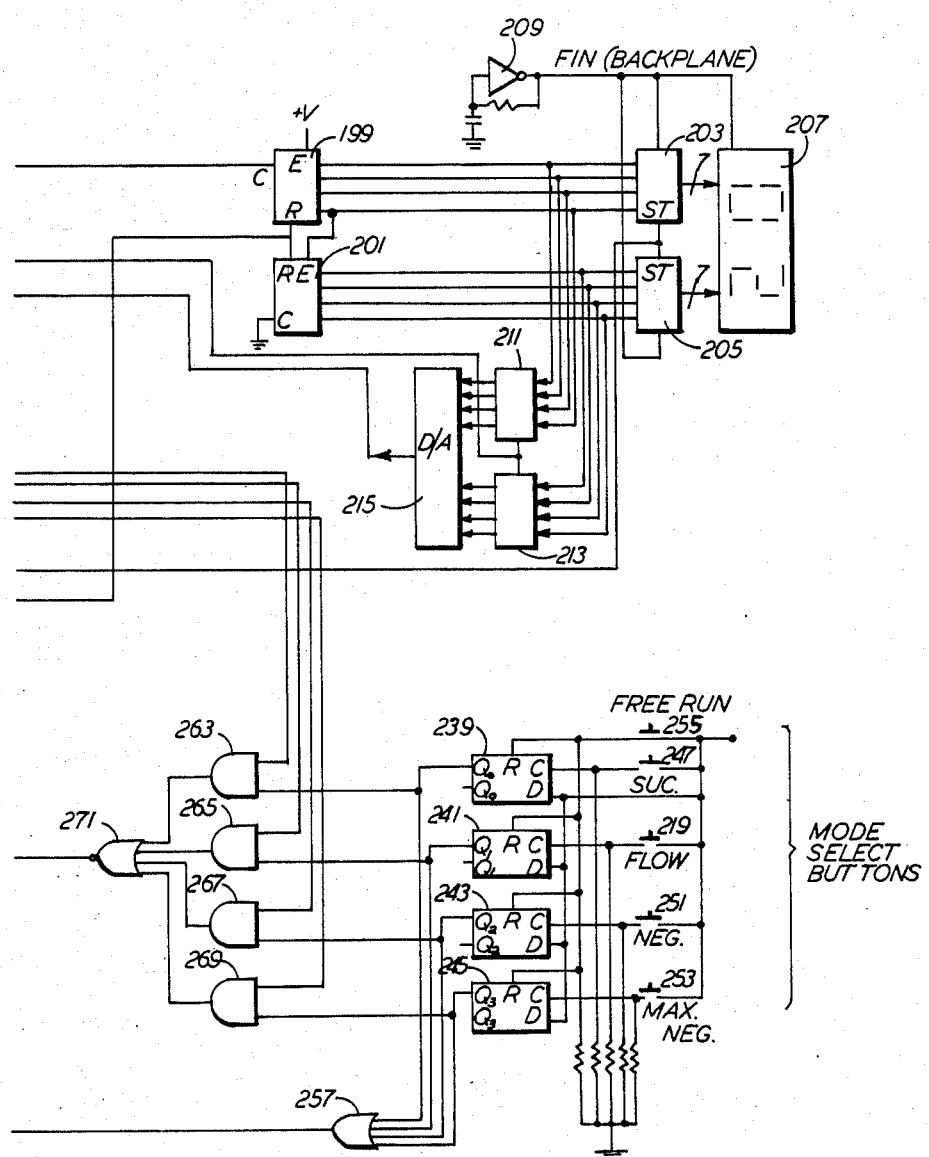

FIG. 8 is a circuit diagram of the embodiment of the invention shown in FIG. 7. Transducers 163, 167 and 169 are shown respectively in FIG. 8 as bridge circuit 191 for measuring suction, a bridge circuit 193 for measuring air flow and a bridge circuit 195 for measuring patient negativity. These bridge circuits are similar in construction and function to transducer 69 in FIG. 2; however, for reasons of economy, the three transducers 191–195 share a common amplifier as discussed below. Thus, in order to reduce the number of amplifiers required, a multiplexer 197 is used for sequentially connecting transducers 191–195 to amplifier $A_7$. Multiplexer 197 is connected to the three transducers by means of connections at the input channels $CH_0$, $CH_1$ and $CH_2$. The outputs of these channels are connected to amplifier $A_7$, amplifier $A_7$ having a positive port which is connected through a resistor $R_2$ to ground and having connected across it a feedback resistor $R_1$. Multiplexer 197 is preferably a CD4052 4-channel differential device. As each channel closes, the small signal generated by the respective bridges is amplified by amplifier $A_7$ and transmitted to a voltage-to-frequency converter (VFC) 198 through a line having a maximum negativity reset switch in series and a resistor from the output side of the switch connected to ground.

The VFC generates a signal whose frequency is linearly related to the DC voltage at its input. The VFC output pulse train from VFC 198 goes to a clock input C of a binary coded decimal (BCD) counter 199; BCD 199 is coupled to a second BCD counter 201. As described below, these counters ultimately control the readout value of each of a pair of digits on a display device 207. The counters are preferably CD4518 devices, and the accumulated BCD count of the VFC pulses over a fixed and predetermined interval of time yields a numerical equivalent of the parameter being measured. The counters are connected respectively to a pair of LCD drivers 203 and 205 which are preferably CD4056 units for the circuit shown. Drivers 203 and 205 are connected to a liquid crystal display (LCD) 207. As with the circuit of FIG. 5, a back plane frequency is needed for the LCD drivers and displays. Therefore, an inverter is used to form a simple oscillator 209 by having a grounded capacitor connected to its input and a feedback resistor connected from its input to its output which in turn is connected to inputs of each of drivers 203 and 205 and the back plane input of LCD displays 207. As in the circuit of FIG. 5, the preferred inverter is a CD40106 inverter. Also, as in the previous circuit, when the digit segments are in phase with the back plane frequency, the segment is OFF; whereas if the frequencies are out of phase, the digit comes ON. The 8 output BITS of counters 199 and 201 are also connected to the inputs of a pair of latches 211 and 213, these preferably being CD4042 latches. The 8 BIT output from latches 211 and 213 are connected to the input of a digital-to-analog converter 215, this being connected to the input of the maximum negativity channel $CH_3$ of multiplexer 197 through a resistor $R_3$. The other switch associated with $CH_3$ is connected to ground through resistor $R_4$.

A decoder 217 whose four output ports are shown as C, D, E and F, is used to identify the four display intervals for the data taken from multiplexer 197. As described in FIG. 6, the High-Low states of decoder 217 coincide with the sequence of closing for the four channels of the multiplexer and are controlled by timing signals A and B emitted by a binary counter 221. Counter 221 is driven by an oscillator 223 whose timing interval dictates that data counters 199 and 201 can only be active for fixed and very accurate intervals of time. Oscillator 223 is made up with a set of resistors, a capacitor and a pair of inverters which are preferably CD40106 inverters. Decoder 217 is preferably a CD4555 decoder, and counter 221 is preferably a CD4520 binary counter.

The data count for each of the measurement intervals is transferred to the input latches of LCD drivers 203 and 205 by a "store" pulse as described below. Serving as the system clock, pulses from oscillator 223 increment the 221 counter to give the A and B timing signals. When A and B are both zero, the zero channel of multiplexer 197 is closed and VFC 198 responds to the voltage from suction transducer 191, and so on.

As indicated above, the system of FIG. 8 alternatively measures suction, air flow and negativity. In order to indicate in which mode the system is at any time, a set of mode indicator lights 225 is provided. Lights 225 are preferably light emitting diodes (LED's). These lights comprise a suction LED 227, an air flow LED 229, a negativity LED 231 and a maximum negativity LED 233. Each LED network includes a transistor whose base is connected to a corresponding output C, D, E or F of decoder 217, a collector to which the LED and a current limit resistor are connected in series, and a grounded emitter. The respective LED's go on when the corresponding output line C, D, E or F goes high. Thus, when A and B both equal zero, the "zero" channel of multiplexer 197 is closed, and the VFC "sees" or is electrically connected to suction transducer 191. This combination of A and B causes the C output of decoder 217 to go high, and this in turn causes suction LED 227 to go on since the transistor of that light has been activated. A and B sequentially close all of the MUX 197 channels and simultaneously energize each of the corresponding lights.

A pair of monostable multivibrators ("one shots") 235 and 237 are connected to the output of oscillator or clock 223. The first monostable 235 has a +TR input connected to the clock and is therefore triggered by the positive edge of the clock signal; monostable 235 provides the "store" pulse which will latch the last data count by counters 199 and 201 as provided by VFC 198.

Monostable 237 has a −TR gate which is triggered by the trailing edge of the "store" signal to provide the "reset" pulse to counters 199 and 201 which sets the counters to zero in preparation for the next data interval, i.e., the next parameter. The sequence of store and reset signals to counters 199 and 201 causes a cyclic readout of the parameters which continues indefinitely unless a particular readout is requested by the attendant who is caring for the patient.

As noted above, the value of maximum negativity is stored in 8 BIT digital form in latches 211 and 213. The output of latches 211 and 213 is transmitted to digital-to-analog converter 215, the output of which is transmitted to comparator $C_1$ as well as to MUX 197. This signal, in analog form, which represents the stored value of maximum negativity, is compared with the new negativity signal generated by transducer 195 and transmitted through channel 2 via amplifier $A_7$ to comparator $C_1$. If the new signal from channel $CH_2$ is larger than the signal from digital-to-analog converter 215, comparator $C_1$ goes high and enables one input of the triple-IN AND gate 219. If the F output of decoder 217, which corresponds to the maximum negativity interval, is also high, the second input of AND gate 219 is enabled. The "store" pulse from one shot 235 enables the third and final input of AND gate 219 causing the output of gate 219 to go high, consequently clocking data latches 211–213. Thus, the most recent negativity signal, which is now the new maximum negativity, becomes the signal stored in latches 211 and 213.

When channel $CH_3$ closes the signal from digital-to-analog converter 215 is transmitted to VFC 198 via amplifier $A_7$, the latter now being configured as a normal unity gain differential amplifier because of the addition of $R_3$ and $R_4$ positioned at the input of channel 3. Counters 199 and 201 record the value transmitted by channel 3 and VFC 198 and this value is displayed on LCD 207.

A set of flip flops 239–245 are used to latch a particular parameter on the display readout. For the circuit shown, these devices are preferably CD4013 "D" type flip flops. The activation of the respective flip flops is controlled by a set of mode select buttons 247–253 which are disposed in transmission lines connected between the voltage source and the clock (C) inputs. A free run button 255 is a switch in the line running from the voltage source to the reset (R) input of flip flops 239–245. An OR gate 257 is connected to the Q outputs of flip flops 239–245. For the system shown, it is preferably a 4-in CD4072 OR gate. The output of OR gate 257 is connected to one input of AND gate 259 and the second input of gate 259 is enabled by NOR gate 271 which is always high in the "free run" mode. The output of AND gate 259 is connected to a switch 261 located in the timing network of system clock 223. AND gate 259 is preferably a CD4081 AND gate, and switch 261 is preferably a CD4066 switch for the system shown.

The activation of OR gate 257 sends AND gate 259 to the high state, thus closing switch 261. The introduction of a smaller resistance in the oscillator time constant of system clock 223 results in a corresponding increase in oscillator frequency. The reason for using this technique is to force timing counter 221 to immediately arrive at the A-B code corresponding to the parameter readout requested; this rather than waiting for the normal time delay associated with the cyclic display of each of the parameters in the normal manner. The normal sequence could add up to a total of several seconds delay before arriving at the desired readout.

One input of each of a set of AND gates 263-269 is connected to the Q outputs of flip flops 239-245; consequently, when a Q signal goes high, one input of the corresponding AND gate 263-269 is enabled. The AND gates are preferably CD4081 2-IN AND gates. A second input of AND gates 263-269 is connected to the correct output of decoder 217. Hence, when the output line of 217 corresponds to the activated mode of a selected one of flip flops 239-245, one of the AND gates 263-269 goes high. If any input of NOR gate 271 is high, its output goes low which in turn disables counter 221 and the system display will "lock" on the selected readout until the free run button 255 is pushed to return the display sequence to its normal mode of operation.

While operating in the "lock" mode, the "store" and "reset" signals occuring with each and every data interval will repeatedly update display 207 with the selected parameter. It should be noted that an automatic return to the "free run" mode can easily be implemented by including a clock pulse of the desired time delay. An OR gate driving the reset ports of 239-245 (switch 247-253 on one input and the clock on the other) would do the resetting function. The resistors connected to the select switches simply reference the flip flop inputs to ground.

Reset of the maximum negativity value stored in latches 211 and 213 is realized by selecting the maximum negativity mode and then depressing the maximum negativity reset button. This opens the line to the VFC allowing the resistor to reference its input to ground; referencing the input of the VFC to ground assures a zero count for the next data cycle.

A timing diagram for the circuit shown in FIG. 8 is shown in the lower left-hand corner of that figure. Although a printer is not shown in conjunction with the system of FIG. 8, the addition of such a unit could be connected using conventional procedures.

One skilled in the art will recognize that the foregoing description has shown preferred embodiments of a very important invention. The invention provides an extremely accurate, compact and effective system for monitoring the drainage of fluids from a cavity such as the pleural cavity. The system can be very comprehensive, providing measurements and controls of many parameters, or it can be somewhat less comprehensive while still providing many measurements and controls more accurate and more complete than exists at the present time. The invention can be practiced in very economical ways, and portions of the inventive system which become contaminated after use can be rendered disposable. In its preferred forms, the invention can be practiced with conventional components using known manufacturing techniques.

The invention has been described in detail with particular emphasis on preferred embodiments thereof. However, it should be understood that variations and modifications within the spirit and scope of the invention may occur to those skilled in the art to which the invention pertains.

I claim:

1. An electronic drainage system for monitoring the air and liquids flowing in a suction conduit from an inaccessible body cavity and for controlling the suction in the suction conduit, said system comprising:

suction control means for controlling the suction in the conduit for the purpose of regulating the air and liquid flow from the cavity, said suction control means maintaining a suction in the conduit;

suction transducer means for monitoring the air pressure in the suction conduit and for generating an actual suction signal whose value is reflective of the actual suction in the conduit; and adjusting means for automatically adjusting said suction control means in increments varying in proportion to deviations in the value of said actual suction signal from a predetermined suction value.

2. The invention according to claim 1 wherein said suction control means comprises air admission means for admitting atmospheric air into the conduit, and said adjusting means comprises means for adjusting said air admission means to control the amount of air admitted into the conduit to regulate the suction in the conduit.

3. The invention according to claim 2 wherein said adjusting means further comprises:

suction selection means for generating a predetermined suction value signal whose value corresponds to the predetermined suction value;

differential integrating means electrically connected to said suction transducer means and to said suction selection means for receiving said actual suction signal and said predetermined suction value signal and for generating a differential integrated signal corresponding to the integral of the difference between said actual suction signal and said predetermined suction value signal; and motor means electrically connected to said differential integrating means and to said air admission means, said motor means adjusting said air admission means according to the value of said differential integrated signal to establish said predetermined suction value in the conduit.

4. The invention according to claim 3 wherein said suction control means comprises variable orifice means including relatively movable members defining a variable orifice in the conduit; and said motor means is operatively connected to at least one of said members to move said members relative to each other to establish an orifice of the size necessary for admitting atmospheric air into the conduit to establish the predetermined suction value in the conduit.

5. The invention according to claim 4 wherein said variable orifice means comprises:

a first member having a first orifice for admitting atmospheric air into the conduit; and a second member movable relative to said first member and having a second orifice, said second member being movable between a position wherein said first and seocnd orifices are substantially out of alignment for substantially blocking the flow of air into the conduit, and a position wherein said first and second orifices are substantially in full alignement for admitting a large amount of air into the conduit, said first and second orifices cooperating to define said variable orifice;

said motor means being connected to said second member for moving said second member relative to said first member according to the value of said differential integrated signal.

6. The invention according to claim 5 wherein said first member further includes a supplemental orifice alignable with said first orifice for venting air from the conduit; and said adjusting means further includes comparison means electrically connected to an electrical source, said source transmitting to said comparison means a positive pressure signal whose value corresponds to a predetermined positive value, to said suction transducer means and to said motor means; said comparison means generating positive pressure vent signal for adjusting said motor means to move said second member to align said supplemental orifice with said first orifice to vent air from the conduit when said actual suction signal exceeds said positive pressure signal.

7. The invention according to claim 1 and further comprising:
patient air flow transducer means for generating an air flow signal whose value is reflective of the rate of flow of air from the body cavity in the conduit.

8. The invention according to claim 7 wherein said patient air flow transducer means comprises:
flap valve means mounted across the conduit between a closed position for blocking the conduit to air flow and a wide open position for enabling a maximum air flow; and
an electrical air flow circuit operatively connected to said flap valve means for generating a patient air flow signal corresponding to the amount of movement of said flap valve means.

9. The invention according to claim 8 and further including means for moving said flap valve means to the closed position when the pressure in the conduit exceeds atmospheric pressure.

10. The invention according to claim 7 and further including patient air flow filtering means for filtering from the signal generated by said air flow transducer means signal components reflective of pressure variations in the conduit caused by normal activity in the body cavity.

11. The invention according to claim 1 and further comprising:
positive pressure vent means for venting air from the conduit when the air pressure in the conduit exceeds a predetermined value, to prevent fluid in the conduit from flowing into the body cavity.

12. The invention according to claim 1 and further comprising:
negativity transducer means for generating an electrical actual negativity signal reflective of the negativity pressure in the body cavity.

13. The invention according to claim 12 and further comprising:
negativity air admission means electrically connected to said negativity transducer means and being actuable for admitting atmospheric air into the conduit when said negativity signal exceeds a predetermined suction value.

14. The invention according to claim 13 and further comprising:
negativity comparison means electrically connected to an electrical source transmitting an electrical signal to said negativity comparison means corresponding to said predetermined suction value, and to said negativity transducer means, for generating a negativity signal to actuate said negativity air admission means when said actual negativity signal exceeds said predetermined suction value.

15. The invention according to claim 14 wherein said negativity air admission means comprises:
valve means for opening and closing a port in the conduit to the atmosphere;
solenoid rod means for moving said valve means between the opening and closing positions; and
solenoid coil means energizable for moving said rod to open said valve means in response to the generation of said negativity signal.

16. The invention according to claim 12 and further comprising:
maximum negativity holding means operatively connected to said negativity transducer means for storing the maximum actual negative signal generated by said negativity transducer means over a period of time.

17. The invention according to claim 38 wherein said maximum negativity holding means includes:
storage means for storing the maximum actual negativity signal generated by said negativity transducer means, and means for replacing any such stored signal with a yet greater actual negativity signal subsequently generated by said negativity transducer means.

18. The invention according to claim 12 and further comprising:
excessive negativity means electrically connected to said negativity transducer means for opening the conduit to the atmosphere when said actual negativity signal exceeds a predetermined value.

19. The invention according to claim 1 and further comprising:
liquid collection means for receiving liquids drained from the body cavity; and
liquid collection transducer means for generating signals reflective of the amount of liquid collected by said liquid collection means.

20. The invention according to claim 19 wherein said liquid collection means comprises a chamber, and the invention further comprises:
dead space limiter means for blocking to air flow from the conduit a portion of said chamber not filled with liquid to expedite air and liquid flow from the body cavity.

21. The invention according to claim 20 wherein said dead space limiter means comprises a receptacle for receiving predetermined quantities of liquid drained from the body cavity, and emptying means actuable for discharging liquid from said receptacle into said chamber when said receptacle has received said predetermined quantity of liquid.

22. The invention according to claim 21 wherein said emptying means comprises:
electrical emptying circuit means having contacts operatively associated with said receptacle, the impedance between said contacts being low when said receptacle has received said predetermined volume of liquid and said impedance being otherwise high;
said emptying means being actuable for discharging liquid from said receptacle when the impedance between said contacts is low.

23. The invention according to claim 22 wherein said contacts are disposed to contact liquid collected in said receptacle only when said receptacle has received said predetermined volume of liquid in said receptacle to assume between them a low resistance, and said contacts assuming between them a high resistance when said receptacle has not received said predetermined volume of liquid, and wherein said electrical emptying circuit means comprises:

resistance means having a resistance value intermediate said high and low resistances between said contacts; and electrical source means for impressing a voltage across said resistance means and across said contacts; and switch means for closing said circuit means to actuate said emptying means when the resistance between said contacts is low.

24. The invention according to claim 23 wherein said switch means comprises:

inverter means electrically connected to said contacts, to said resistance means, and to said emptying means; said inverter means having a low state wherein it does not transmit a signal to actuate said emptying means when the resistance between said contacts is high, and said inverter means having a high state wherein it transmits an energizing signal to actuate said emptying means when the resistance between said contacts is low.

25. The invention according to claim 24 wherein said emptying means comprises:

door means actuable for opening said receptacle to discharge the liquid contents of said receptacle; and solenoid means connected to said door means for actuating said door means in response to energization of said solenoid means, said solenoid means being electrically connected to said inverter means and being energized in response to the transmission of said energizing signal by said inverter means.

26. The invention according to claim 24 wherein said switch means further comprises:

transistor means for transmitting an actuating signal to said emptying means in response to the transmission of an energizing signal by said inverter means.

27. The invention according to claim 24 and further comprising:

door means actuable for opening said receptacle to discharge the liquid contents of said receptacle;

solenoid means connected to said door means for actuating said door means in response to energization of said solenoid means;

biassing means for closing said door means when said solenoid is de-energized;

transistor means for transmitting an actuating signal to said solenoid means to energize said solenoid means in response to the transmission of an energizing signal by said inverter means; and delay means for maintaining the energization of said solenoid means to maintain said door means open for emptying said receptacle.

28. The invention according to claim 19 wherein said liquid collection transducer means comprises volume transducer means for generating volume signals reflective of the volume of liquid collected in said liquid collection means.

29. The invention according to claim 19 wherein said liquid collection transducer means comprises weight transducer means for generating weight signals reflective of the weight of liquid collected in said liquid collection means.

30. The invention according to claim 1 and further comprising:

temperature transducer means for generating signals reflective of the temperature of fluids in the body cavity.

31. The invention according to claim 1 wherein said adjusting means comprises:

set point selection means for establishing a reference signal reflective of said predetermined suction value; and error signal generating means electrically connected to said set point selection means, to said suction transducer means, and to said suction controlling means, for generating adjusting signals to said suction controlling means to adjust said suction controlling means to bring the actual suction signal within a predetermined limit from the predetermined suction value.

32. The invention according to claim 1 wherein said suction control means comprises:

variable orifice means for controlling the suction in the conduit by admitting atmospheric air into the conduit, said variable orifice means including relatively movable members defining a variable orifice in the conduit; and wherein said adjusting means comprises:

means for moving at least one of said members to establish an orifice of the size necessary for admitting atmospheric air into the conduit to establish the predetermined value of suction in the conduit.

33. The invention according to claim 32 wherein said suction control means further comprises:

suction air flow measuring means for measuring the rate of atmospheric air flow through said variable orifice into the conduit.

34. The invnetion according to claim 33 wherein said suction air flow measuring means comprises:

flap valve means movably mounted across said variable orifice, said flap valve means being movable by an amount reflective of the air flow rate through said orifice, and electrical circuit means for generating a suction air flow signal corresponding to the amount of movement of said flap valve means.

35. The invention according to claim 34 wherein said suction control means comprises:

a first member having a first orifice for admitting atmospheric air into the conduit, said flap valve means being mounted for movement between a position closing said first orifice and a position opening said first orifice corresponding to a maximum flow of air through said first orifice; and a second member movable relative to said first member and having a second orifice, said second member being movable between a position wherein said first and second orifices are substantially out of alignment for substantially blocking the flow of air into the conduit, and a position wherein said first and second orifices are substantially in full alignment for admitting a large amount of air into the conduit, said first and second orifices cooperating to define said variable orifice according to the extent said first and second orifices overlap; said adjusting means being operatively connected to said second member for moving said second member relative to said first member according to deviation of said actual suction signal from the predetermined suction value.

36. The invention according to claim 35 wherein said first member further comprises a supplemental orifice, said second member being movable to align said second orifice with said supplemental orifice for venting gas from the conduit when the air pressure in the conduit exceeds atmospheric pressure by a predetermined amount.

37. The invention according to claim 1 wherein said adjusting means comprises:
   suction selection means for generating a suction signal whose value corresponds to the predetermined suction value;
   differential integrating means electrically connected to said suction transducer means and to said suction selection means for receiving said actual suction signal and said suction signal, and for generating a differential integrated signal corresponding to the integral of the difference between said suction selection signal and said actual suction signal; and
   motor means operatively connected to said suction control means and to said differential integrating means for adjusting said suction control means according to the value of said differential integrated signal to establish said predetermined suction value in the conduit.

38. The invention according to claim 37 and further including positive pressure vent means for venting air from the conduit when the air pressure in the conduit exceeds a predetermined positive value to prevent air in the conduit from flowing into the body cavity, said positive pressure vent means comprising:
   comparison means electrically connected to an electrical source, said source transmitting to said comparison means a positive pressure signal whose value corresponds to said predetermined positive value, to said suction transducer means, and to said suction regulator means; said comparison means generating a positive pressure vent signal for adjusting said suction control means to vent air from the conduit when said actual suction signal exceeds said positive pressure vent signal.

39. The invention according to claim 1 and further including suction flow filtering means for filtering from the signal generated by said suction transducer means signal components reflective of short term pressure variations.

40. The invention according to claim 1, 2, 12, 19, 30, 32, 34, 37 or 3, and further comprising display means electrically connected to the respective transducer means for displaying the signals generated by the respective transducer means and the signal corresponding to said predetermined suction value.

41. An electronic drainage system for monitoring and controlling the flow of fluid in a suction conduit for an inaccesible body cavity, said system comprising;
   adjusting means for generating signals whose values are reflective of a predetermined suction value;
   suction transducer means for generating actual suction signals whose values are reflective of the suction in the conduit;
   suction control means operatively connected to said adjusting means and to said suction transducer means for admitting atmospheric air into the conduit to regulate the suction in the conduit according to the value of said adjusting means signals and of said actual suction signals while maintaining air suction in the conduit and suction air flow transducer means for generating suction air flow signals whose values are reflective of the air flow into the conduit;
   patient air flow transducer means associated with said suction control means for generating patient air flow signals whose values are reflective of the rate of patient air flow in the conduit;
   negativity transducer means associated with said patient air flow transducer means for generating actual negativity signals whose values are reflective of the negativity pressure in the body cavity;
   liquid collection means for collecting liquid drain from the body cavity, and liquid collection transducer means for generating liquid collection signals whose values are reflective of the amount of liquid collected by said liquid collection means; and
   temperature transducer means for generating temperature signals whose values are reflective of the temperature of fluid in the body cavity;
   multiplexer means electrically connected to said at least two signal generating means for alternatively transmitting signals from said at least two signal generating means;
   display means for displaying in intelligible form symbols in response to signals transmitted to said display means; and
   signal processing means electrically connected to said multiplexer means for processing signals transmitted by and received from said multiplexer means into signals readable by said display means, and for transmitting processed signals to said display means.

42. The invention according to claim 41 wherein said signal generating means each generate analog signals, said display means comprises digital display means for displaying said signals in response to digital signals transmitted to said digital display means, and said signal processing means comprises analog-to-digital converter means for converting analog signals received from said signal generating means into digital signals readable by said digital display means.

43. The invention according to claim 41 and further comprising:
   parameter locking means electrically connected to said multiplexer means for locking said multiplexer means to transmit signals from only a selected one of said signal generating means to said signal processing means.

44. The invention according to claim 43 and further comprising:
   parameter indicating means electrically connected to said parameter locking means for indicating the selected one of said signal generating means locked by said multiplexer means.

45. The invention according to claim 44 wherein said display means comprises a numerical display for displaying a number to which said selected signal corresponds.

46. The invention according to claim 41 wherein said displays means comprises a plurality of numerical display electrically connected to said signal generating means respectively, for displaying a number to which the signal generated by said respective signal means corresponds.

47. The invention according to claim 41 wherein said signal processing means comprises an amplifier for amplifying the respective signals transmitted to said amplifier by said multiplexer means.

48. The invention according to claim 41 wherein said liquid collection transducer means includes weight transducer means for generating weight signals whose values are reflective of the weight of the liquid collected by said liquid collection means.

49. The invention according to claim 41 wherein said liquid collection transducer means includes volume transducer means for generating volume signals whose values are reflective of the volume of liquid collected by said liquid collection means 50. An electronic drainage system for monitoring gases and liquids flowing in a suction conduit from a pleural cavity and for controlling the suction in the suction conduit, said system comprising:

suction control means for controlling the suction in the conduit for the purpose of regulating the flow of gas and liquid from the pleural cavity, said suction control means including air admission means for admitting atmospheric air into the conduit while maintaining a suction in the conduit; suction transducer means for monitoring the pressure in the suction conduit and for generating actual suction signals whose values are reflective of the suction in the conduit;

positive pressure vent means for venting gas from the conduit when the gas pressure in the conduit exceeds atmospheric pressure by a predetermined amount;

patient air flow transducer means for generating air flow signals whose values are reflective of the rate of air flow from the pleural cavity in the conduit;

patient negativity transducer means for generating actual negativity signals whose values are reflective of the negativity pressure in the pleural cavity;

excessive negativity means for admitting atmospheric air into the conduit when the actual negativity is less than a predetermined value;

liquid collection means for collecting liquid drained from the pleural cavity;

multiplexer means electrically connected to said suction transducer means, said patient air flow transducer means and to said patient negativity transducer means, for alternatively transmitting the signals generated by said respective transducer means;

signal processor means electrically connected to said multiplexer means for processing signals transmitted by said multiplexer means; and display means electrically connected to said signal processor means for displaying in intelligible form signals corresponding to the signals transmitted by signal processor means.

51. The invention according to claim 50 and further comprising:

maximum negativity holding means electrically connected to said signal processor means for receiving and retaining actual negativity signals generated by said negativity transducer means whose value exceeds that of previously generated actual negativity signals.

52. The invention according to claim 51 wherein said maximum negativity holding means comprises latching means for storing maximum negativity signals;

and wherein said system further comprises comparison means electrically connected to said multiplexer means and to said latching means for comparing actual suction signals transmitted by said multiplexer means with the maximum negativity signal stored in said latching means, and for generating a new maximum negativity signal when an actual suction signal exceeds the stored maximum negativity signal, said latching means storing the actual suction signal in response to the generation of a new maximum negativity signal.

53. The invention according to claim 52 and further comprising:

AND gate means having high and low states; and said AND gate means having an output connected to said latching means, and first, second and third inputs;

decoder means having a maximum negativity gate connected to the first input of said AND gate means, said maximum negativity gate transmitting a decoder signal to the first input of said AND gate means in response to maximum negativity timing signals;

oscillator means for periodically transmitting maximum negativity timing signals to said decoder means; and counter control means electrically connected to the second input of said AND gate means for periodically generating store signals;

and wherein said comparison means has an output port electrically connected to the third input of said AND gate means;

said AND gate means assuming its high state in response to the transmission of a decoder signal, a store signal and a new maximum negativity signal to its respective first, second and third inputs; and said latching means replacing a stored maximum actual negativity signal with the new maximum negativity signal in response to said AND gate assuming its high state.

54. The invention according to claim 51 for arbitrarily resetting said maximum negativity holding means to a predetermined value.

55. The invention according to claim 51 wherein said maximum negativity means is further electrically connected to said multiplexer means for periodically receiving signals generated by said negativity transducer means.

56. The invention according to claims 16 or 51 and further comprising means for arbitrarily resetting said maximum negativity holding means.

57. The invention according to claims 41, 50 or 55 and further comprising processor-printer means electrically connected to said multiplexer means for periodically receiving signals transmitted by said multiplexer means and for periodically printing values corresponding to the respective values of said received signals in intelligible form.

58. The invention according to claims 1, 41 or 50 and further comprising an electrical battery for energizing said system, and low battery voltage warning means connected to said battery for generating a warning signal when the voltage of said battery falls below a predetermined value.

59. The invention according to claims 41, or 50 and further comprising electrical battery means for energizing said system, low battery voltage warning means connected to said battery means and to said display means for transmitting a warning signal to said display means for indicating when the voltage of said battery means falls below a predetermined value.

60. The invention according to claim 50 wherein said signal processor means comprises amplifier means for amplifying signals generated by said respective transducer means and transmitted by said multiplexer means.

61. The invention according to claim 60 wherein said processor means further comprises:
- voltage-to-frequency converter means connected to said amplifier means for receiving signals amplified by said amplifier means; and
- first counter means electrically connected to said voltage-to-frequency means for generating count signals according to the frequency of said amplified signals;
- said display means being connected to said first counter means for generating in intelligible form, signals according to the count signals generated by said first counter means.

62. The invention according to claims 50 or 61 and further comprising system clock and timing function means electrically connected to said multiplexer means and to said signal processor means for generating timing signals to control the timing and sequencing of the operations of said multiplexer means and of said signal processor means.

63. The invention according to claim 61 and further comprising system clock and timing function means electrically connected to said multiplexer means and to said signal processor means for generating timing signals to control the timing and sequencing of the operations of said multiplexer means and of said signal processor means, said system clock and timing function means comprising:
- decoder means electrically connected to said multiplexer means for adjusting said multiplexer means to transmit actual signals from said suction transducer means, in response to the reception of timing signals by said decoder means;
- second counter means electrically connected to said decoder means for sending timing signals to said decoder means in response to timing pulses; and
- oscillator means for sending timing pulses to said second counter means to cause said second counter means both to actuate said decoder means and to cause said multiplexer means to transmit actual suction signals from said suction transducer means.

64. The invention according to claim 50 and further comprising:
- mode indicator means electrically connected to said display means for indicating the type of signal being displayed on said display means.

65. The invention according to claim 63 wherein said decoder means includes a plurality of gates corresponding to the respective transducer means, the respective gates having high states when said multiplexer means transmits signals from the transducer means to which the respective gates correspond, and said system comprising:
- mode indicator means electrically connected to the respective gates of said decoder means, said mode indicator means generating intelligible signals reflective of which of said gates is in its high state for indicating the transducer means from which said multiplexer means is transmitting signals to said display means.

66. The invention according to claim 64 or 65 wherein said mode indicator means comprises mode indicator lights and said intelligible signals comprises illumination of the respective lights.

67. The invention according to claim 63 and further comprising:
- counter control means electrically connected to said oscillator means and to said first counter means for controlling said first counter means, said counter control means generating store signals to said first counter means in response to timing pulses from said oscillator means to limit the number of count signals generated by said first counter means, and said counter control means generating reset signals in response to the termination of said store signals to reset said first counter means in preparation for the next signal to be transmitted by said multiplexer means.

68. The invention according to claim 50 or 51 and further comprising:
- locking means for locking said multiplexer means to transmit a particular one of its input signals for display on said display means, said locking means comprising:
- system clock and timing function means electrically connected to said multiplexer means and to said signal processor means for generating timing signals to control the timing and sequencing of said multiplexer means and of said signal processor means;
- voltage source means;
- parameter transmission means energizable for alternatively transmitting signals corresponding to signals transmitted by said multiplexer means;
- mode select means actuable for selectively connecting said parameter transmission means to said voltage source means to energize the selected parameter transmission means; and
- clock connection means connecting said parameter transmission means to said system clock and timing function means; said clock connection means being actuable in response to actuation of the respective mode selection means to increase the frequency of the generation of timing signals by said system clock and timing function means to decrease the time when said multiplexer means next transmits the signal to which said mode select means corresponds.

69. The invention according to claim 1, 41 or 50 wherein said suction control means maintains a fixed value of suction in the conduit.

* * * * *

UNITED STATES PATENT AND TRADEMARK OFFICE
CERTIFICATE OF CORRECTION

PATENT NO. : 4,654,029

DATED : March 31, 1987

INVENTOR(S) : Nicholas F. D'Antonio

It is certified that error appears in the above-identified patent and that said Letters Patent is hereby corrected as shown below:

Column 9, lines 10 to 11, change "processor 21 and to display 23" to

— —processor 7 and to display 9— —

Signed and Sealed this

Nineteenth Day of December, 1989

Attest:

JEFFREY M. SAMUELS

*Attesting Officer*  *Acting Commissioner of Patents and Trademarks*